(12) United States Patent
Maki et al.

(10) Patent No.: US 6,379,347 B1
(45) Date of Patent: Apr. 30, 2002

(54) ENERGY IRRADIATION APPARATUS

(75) Inventors: Shin Maki; Shigeki Ariura; Shigenobu Iwahashi, all of Kanagawa-ken (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/320,630

(22) Filed: May 27, 1999

(30) Foreign Application Priority Data

May 28, 1998 (JP) ............................................ 10-148023
Jun. 12, 1998 (JP) ............................................ 10-165423

(51) Int. Cl.7 ............................................ A61B 18/18
(52) U.S. Cl. ............................................ 606/17; 606/18
(58) Field of Search .............................. 606/41, 46, 15, 606/10, 16, 17, 18, 7, 14, 19; 607/88, 92, 93; 378/65; 600/439

(56) References Cited

U.S. PATENT DOCUMENTS

| 4,529,267 A | * | 7/1985 | Nishioka | 600/437 |
|---|---|---|---|---|
| 4,849,859 A | * | 7/1989 | Nagasawa | 362/573 |
| 4,932,956 A | | 6/1990 | Reddy et al. | |
| 4,932,958 A | | 6/1990 | Reddy et al. | |
| 5,036,855 A | * | 8/1991 | Fry et al. | 600/439 |
| 5,160,337 A | | 11/1992 | Cosman | |
| 5,207,672 A | | 5/1993 | Roth et al. | |
| 5,292,320 A | | 3/1994 | Brown et al. | |
| 5,380,317 A | * | 1/1995 | Everett | 606/15 |
| 5,496,308 A | | 3/1996 | Brown et al. | |
| 5,596,989 A | * | 1/1997 | Morita | 600/437 |
| 5,748,700 A | * | 5/1998 | Shepard et al. | 378/65 |
| 5,792,215 A | * | 8/1998 | Martin et al. | 607/89 |
| 5,866,914 A | * | 2/1999 | Jones | 250/505.1 |
| 5,916,210 A | * | 6/1999 | Winston | 606/7 |
| 6,134,003 A | * | 10/2000 | Tearney et al. | 356/345 |
| 6,152,951 A | * | 11/2000 | Hashimoto et al. | 607/92 |

FOREIGN PATENT DOCUMENTS

| EP | 659387 | 6/1995 |
|---|---|---|
| EP | 0 673 627 | 9/1995 |
| EP | 821916 | 2/1998 |
| FR | 2681522 | 3/1993 |
| WO | 92/04934 | 4/1992 |
| WO | 93/03678 | 3/1993 |
| WO | 93/04727 | 4/1993 |

* cited by examiner

Primary Examiner—Michael Peffley
(74) Attorney, Agent, or Firm—Burns, Doane, Swecker & Mathis, LLP

(57) ABSTRACT

An side irradiating type laser ray irradiation apparatus for irradiating a tissue with a laser ray having a deep transmitting capability for the purpose of treating, for example, Benign Prostatic Hyperplasia, cancer or other tumors. The apparatus includes an irradiating unit for reflecting the laser ray, a transporting device for transporting the irradiating unit, and an interlocking device for changing the irradiation angle of the laser ray in correspondence with the movement so that the laser ray radiated from the moving irradiating unit always passes through the same point. Since the laser ray constantly passes through a point in a deep area of the tissue, it is capable of effectively heating only the deep lesional region.

20 Claims, 17 Drawing Sheets

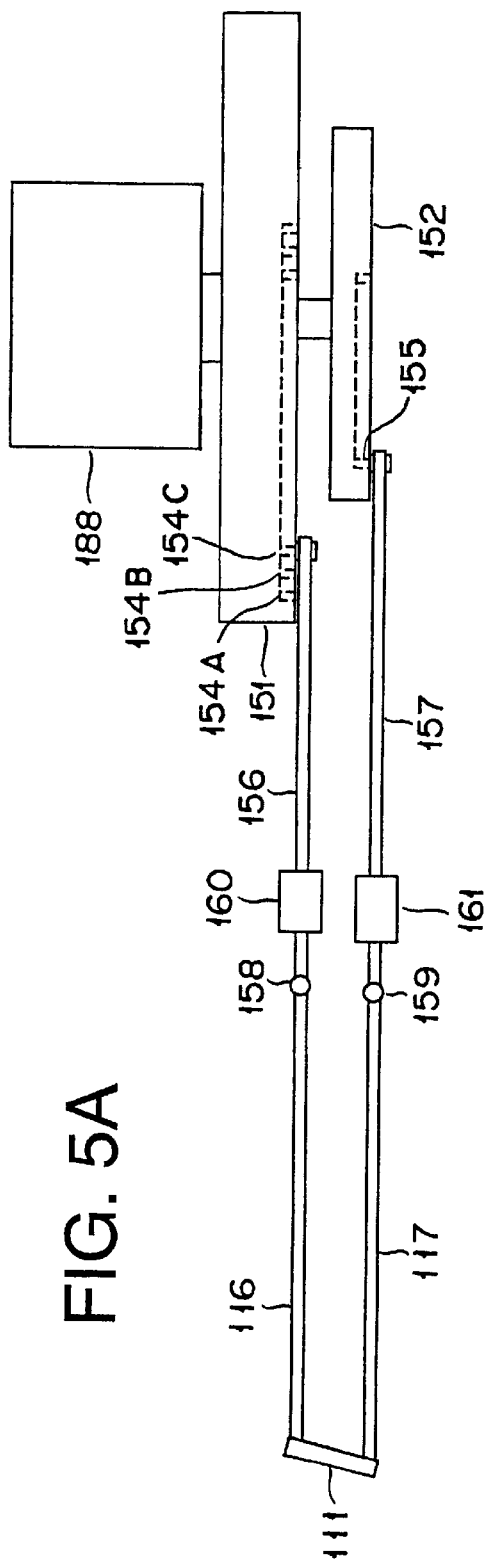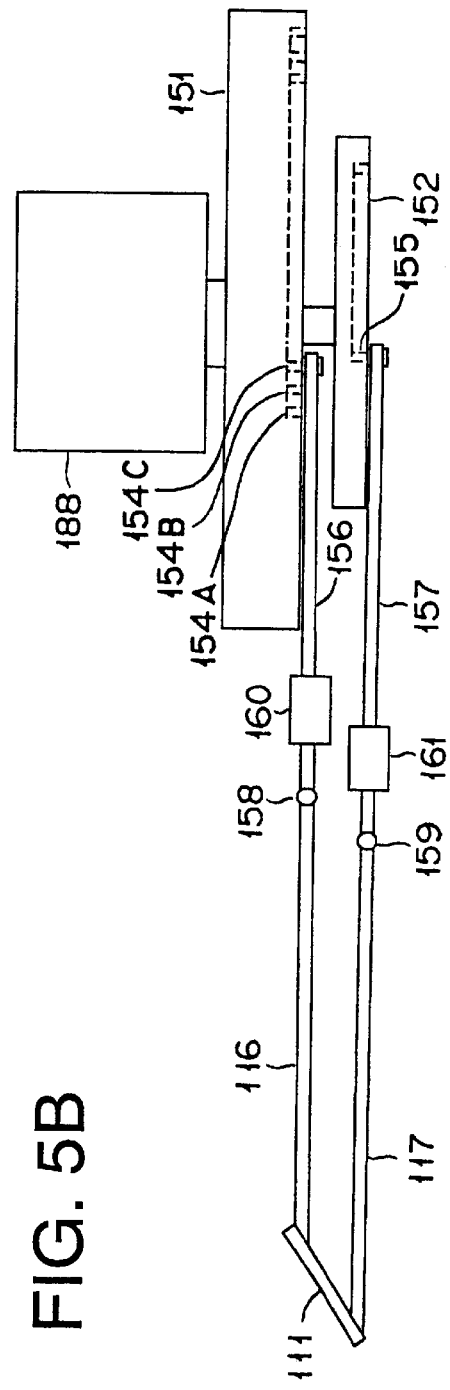
FIG. 5A
FIG. 5B

ENERGY IRRADIATION APPARATUS

BACKGROUND OF THE INVENTION

1. Field of the Invention

The invention relates to an apparatus that is inserted into a lumen such as a blood vessel, urethra or abdominal cavity to irradiate a tissue with an energy such as a laser ray or an ultrasonic ray that is capable of reaching deep into the tissue.

2. Description of the Related Art

It is well known that an energy irradiation apparatus of a long shape that can be inserted into the body utilizing a celom or a small incision is useful for irradiating a lesional region to reduce or to eliminate it through alteration, necrosis, coagulation, cauterization or evaporation for the treatment.

The technique in general is to irradiate directly a lesional region located at a surface layer of a tissue or its proximity. There is another technique of irradiating a tissue with a purpose of curing of a lesional region located deep in the tissue, or a deep lesional region. However, in order to reduce or to eliminate a tissue of the deep lesional region, it requires a relatively strong energy, which may cause a damage to the surface layer.

U.S. Pat. Nos. 5,292,320 and 5,496,308 disclose irradiation apparatuses for curing Benign Prostatic Hyperplasia by means of a laser ray as an irradiating energy. In the irradiation apparatuses, laser rays radiated from a plurality of irradiating units located at different positions converge on a target point in the deep lesional region to generate a sufficient amount of heat to reduce or to eliminate the ailing tissue. Thus, the temperature becomes higher than those of other areas where laser rays are not concentrated. However, since the paths of the laser rays are fixed, the temperature of a surface layer and its proximity where laser rays are not overlapped becomes relatively higher than those of other areas where any laser rays are not transmitted. This phenomenon affects the protection of the surface layer. Therefore, it is circumstantially difficult to heat the deep lesional region to a temperature necessary for reducing or removing the tissue of the deep lesional region while minimizing damages to the surface layer.

Also known is the leksell gamma knife, an apparatus used for the treatment of encephalic diseases utilizing gamma ray as a source of irradiating energy. In the apparatus, gamma rays radiated simultaneously from a plurality of irradiating units arranged in a semispherical pattern converge on a target point in the deep lesional region to bring a necrosis to the ailing tissue. However, the gamma rays also affect tissues existing along the paths of the rays as the rays pass through. Therefore, it is circumstantially difficult with such an apparatus to reduce or to remove the ailing tissue in the deep lesional region while minimizing the damages to the surface layer, also.

SUMMARY OF THE INVENTION

An object of the invention is to provide an apparatus that is capable of effectively radiating an energy to a target region, particularly a region located in a deep area, while easily and securely preventing damages to a normal tissue, particularly a normal tissue in the surface layer.

Another object of the invention is to provide a method of treating Benign Prostatic Hyperplasia, while easily and securely preventing damages to a normal tissue, particularly a normal tissue in the surface layer.

One aspect of the invention is an energy irradiation apparatus includes an irradiating unit, a transporting device and an interlocking device. The irradiating unit radiates an energy with a deep transmitting capability against a tissue. The transporting device transports the irradiating unit within a predetermined area. The interlocking device changes irradiation angle in response to transportation of the irradiating unit so that the energy radiated by the moving irradiating unit always passes through an area which is smaller than the predetermined area.

Another aspect of the invention is a treatment method for Benign Prostatic Hyperplasia by irradiating a first area existing in a lesional region of prostate while moving an irradiating unit for radiating laser ray with a deep transmitting capability against a tissue within a second area which is larger than the first area and changing irradiating angle of the laser ray in correspondence to motion of the irradiating unit.

The objects, characteristics, and advantages of this invention other than those set forth above will become apparent from the following detailed description of the preferred embodiments, which refers to the annexed drawings.

BRIEF DESCRIPTION OF THE DRAWINGS

FIGS. 5A and 5B are drawings for describing the operating principle of the laser ray irradiation apparatus;

DETAILED DESCRIPTION OF THE EMBODIMENTS

The embodiments of this invention will be described below with reference to the accompanying drawings.

Embodiment 1

Figure 1:
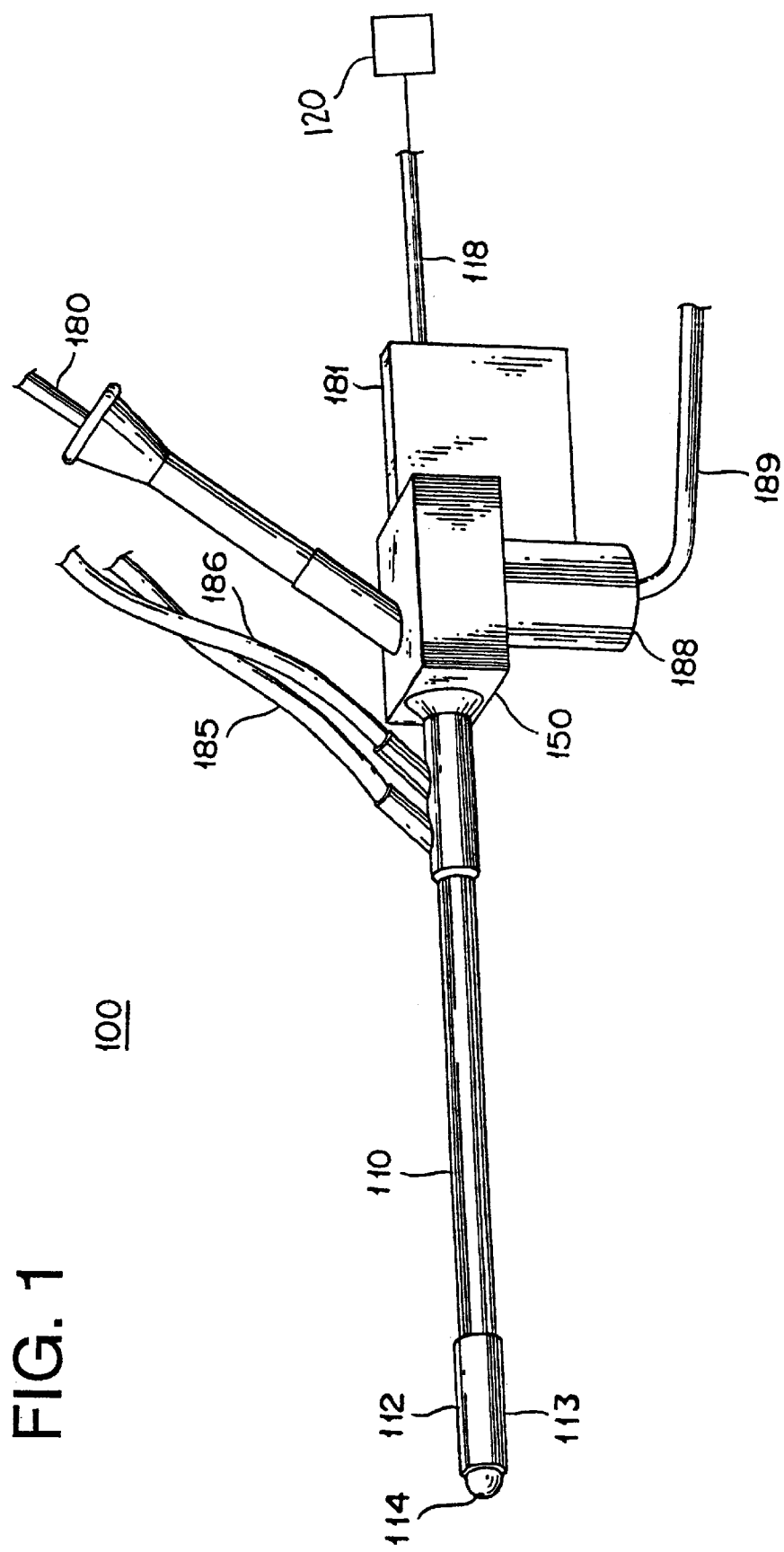
FIG. 1 is a perspective view of a laser ray irradiation apparatus according to a first embodiment of the present invention.
Figure 2:
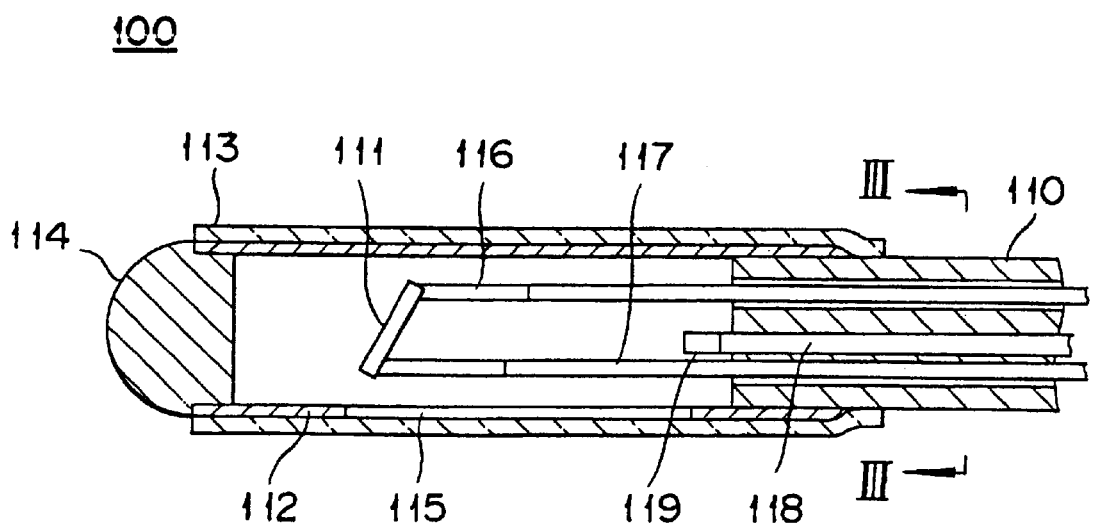
FIG. 2 is a cross section of a distal end of the laser ray irradiation apparatus.

An energy irradiation apparatus 100 shown in FIG. 1 and FIG. 2 is a lateral irradiating type laser ray irradiation apparatus for irradiating a tissue with a laser ray for the purpose of treating, for example, Benign Prostatic Hyperplasia, cancer or other tumors.

The laser ray irradiation apparatus 100 includes a body 110 having a long shape, an irradiating unit 111 that radiates laser ray, and a housing 112 that contains the irradiating unit 111 and is connected the distal end of the body 110.

The housing 112 consists of a hard tubular body having a window 115 for laser ray irradiation. The surface of the housing 112 is covered with a covering member 113 made of a laser ray transmitting material. The distal end of the housing 112 is sealed with a cap 114.

The irradiating unit 111 is connected to arms 116, 117. The arms 116, 117 support the irradiating unit 111 within the housing 112 in such a way as to be able to slide freely, and function as the transportation means for transporting it in the axial direction of the body 110. The arms 116, 117 are connected to a drive unit 150 (interlocking device), which is arranged on the proximal end of the apparatus 100. The drive unit 150 is connected to a motor (electrical drive device) 188 to which electric power is supplied via a cable 189. Therefore, the tilt angle of the irradiating unit 111 can be changed interlocked with the axial position of the body of the irradiating unit 111.

An optical fiber (energy transmitting member) 118 is provided inside the body 110. A lens 119 is provided at the distal end of the optical fiber 118. The lens 119 is an optical element for converging laser ray into collimated ray. The optical fiber 118 passes through a shock absorbing device 181 to be connected to a laser ray generating apparatus 120, which generates laser ray, via a connector. The shock absorbing device 181 that contains the optical fiber 118 forming a loop absorbs the motion and/or a load of the optical fiber 118.

The apparatus 100 further includes a removable endoscope 180. The endoscope 180 is inserted from the proximal end toward the distal end of the apparatus 100. A guide light for observation by the endoscope 180 is generated by another light source such as He-Ne laser, with which the laser ray generating apparatus 120 is equipped, and is transmitted through the optical fiber 118. Therefore, it allows the operator to, observe the surface layer of the position where it is irradiated with the laser ray, to position the housing properly based on the observation of the endoscope, and visual confirmation of the laser irradiation position. Since the irradiated surface can be continuously observed during a laser irradiation operation, the irradiation condition can be easily optimized based on the actual condition.

Figure 3:
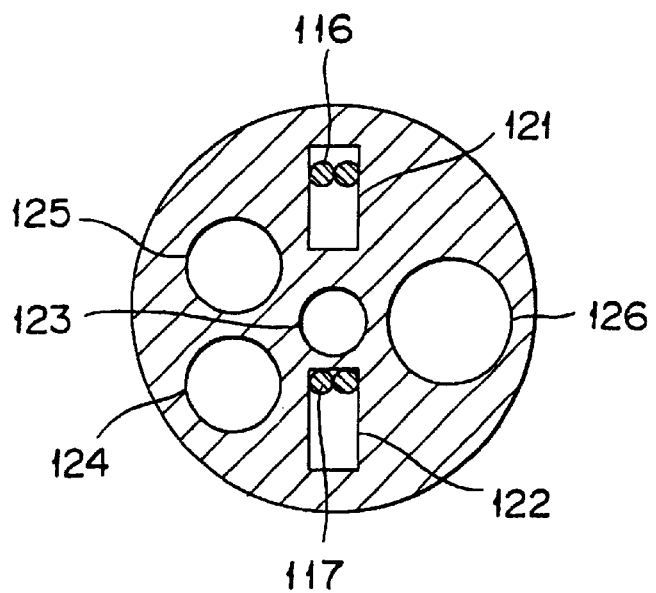
FIG. 3 is a cross section along the line III—III of FIG. 2.

As shown in FIG. 3, the body 110 of the apparatus 100 is equipped with working lumens 121, 122 into which arms 116, 117 can be inserted in such a way as to be able to slide freely. The working lumens 121, 122 are provided in parallel with the axis of the body 110. The body 110 is further equipped with a lumen 123 for the optical fiber 118 as well as lumens 124, 125 for,feeding and discharging the coolant. The coolant is used for alleviating the heat generated in the housing 112 due to the laser ray, and to cool the surface layer of the tissue that contacts with the covering member 113. The lumens 124, 125 are respectively connected to feeding and discharging tubes 185 and 186 (see FIG. 1) of a coolant circulating device via an inlet connector and an outlet connector provided in the apparatus. In order to prevent the coolant from flow backward toward the proximal end, it is preferable that each of the lumens 121, 122, 123, and 126 has a check valve. It is possible to use the working lumens 121, 122 for coolant feeding and discharging as well. Physiological saline is used as a preferable coolant, because any leakage of such a coolant into a tissue causes least damage. The body 110 also has a lumen 126 for the endoscope 180 (see FIG. 1).

Figure 4A:
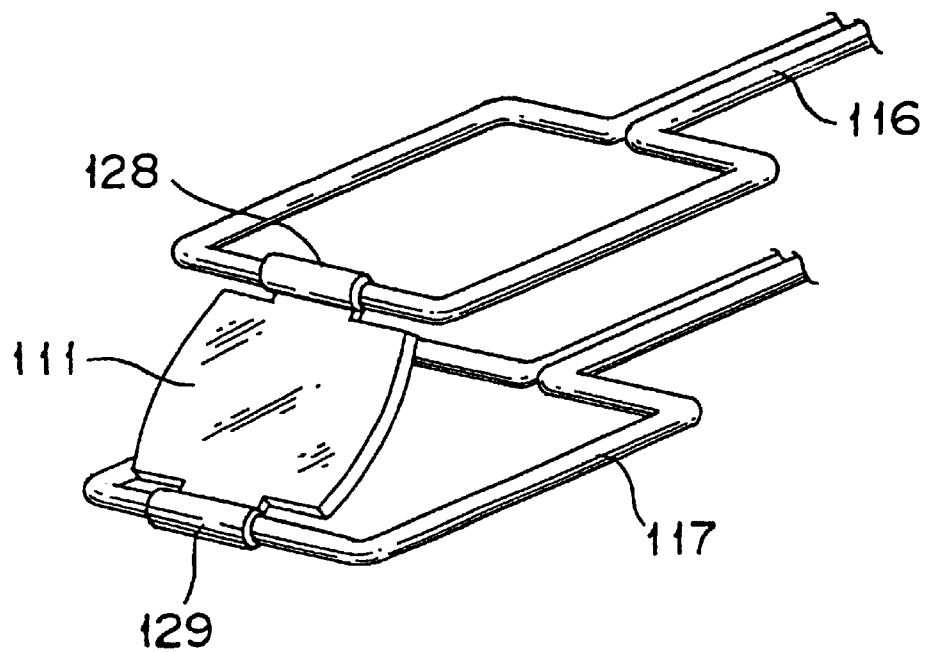
FIGS. 4A and 4B are a perspective view and a side view respectively for describing structures of an irradiating unit and arms of the laser ray irradiation apparatus.
Figure 4B:
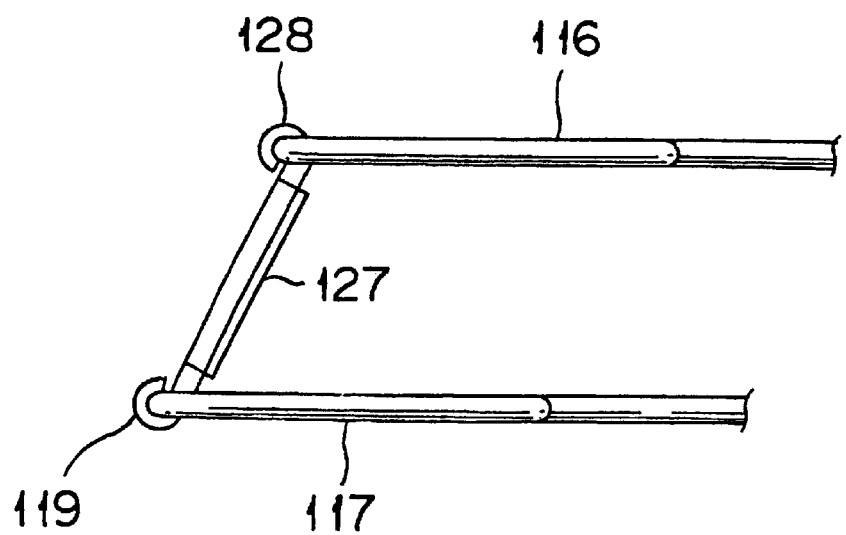

As shown in FIGS. 4A and 4B, the irradiating unit 111 includes a plate that contains a flat reflecting surface 127 to reflect the laser ray as well as connecting parts 128, 129 formed on the backside of the reflecting surface 127. The irradiating unit 111 is connected rotatably to arms 116, 117 via the connecting parts 128, 129.

Next, transporting mechanisms and irradiating angle changing mechanisms of the irradiating unit 111 will be explained referring to FIGS. 5A, 5B and 6.

As shown in FIGS. 5A and 5B, the irradiating angle of the irradiating unit 111 and the axial movement of the arms 116, 117 are interlocked and they are driven by the drive unit 150. More specifically, a groove cam 151 with grooves 154A, 154B, 154C and a groove cam 152, which is smaller than the groove cam 151 and has a groove 155, are provided inside the drive unit 150, and the rotating shaft 153 of the groove cams 151, 152 is connected to the shaft of the motor 188, which is the electrical drive unit. The arms 116, 117 are moved axially and linearly by means of the groove cams 151, 152.

Figure 6:
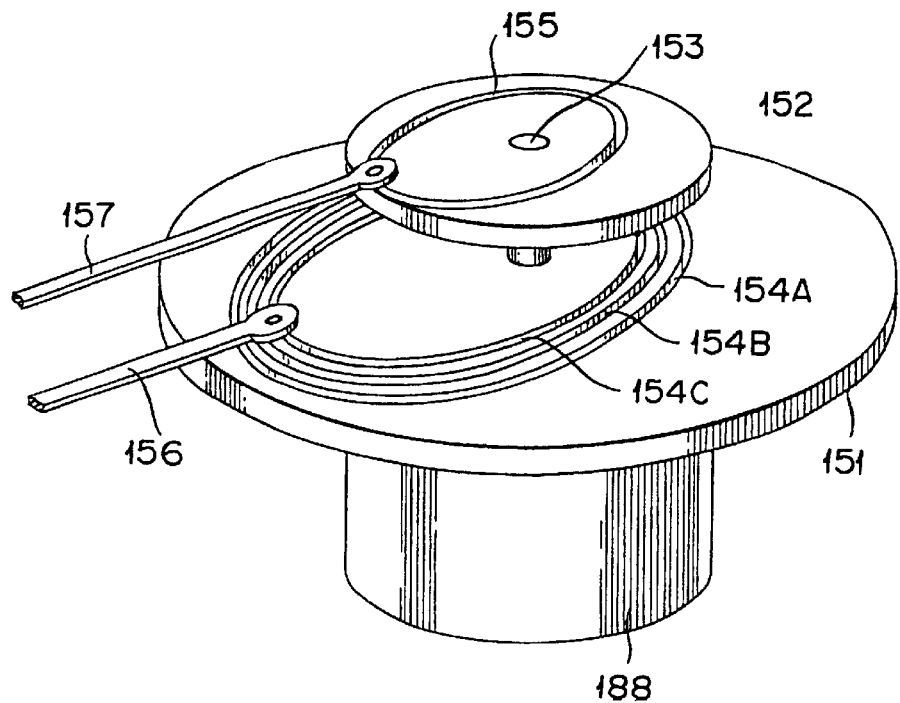
FIG. 6 is a perspective view for describing a drive unit of the laser ray irradiation apparatus.

As shown in FIG. 6, the grooves 154A, 154B, 154C and the groove 155 are oval or elliptic in shape. Extension arms 156 and 157 are engaged with one of the elliptical grooves 154A, 154B, 154C and the elliptical groove 155 in a movable manner, respectively. The groove cams 151, 152 are rotated around the rotating shaft 153 by the motor 188. The rotating shaft 153 is eccentrically situated relative to the grooves 154, 155. Thus, the extension arms 156, 157 as well as arms 116, 117 repeat linearly reciprocating motions in accordance with the rotations of the groove cams 151, 152. The motion range of the arm 116 and the extension arm 156 is larger than that of the arm 117, 157. Therefore, the irradiating angle of the irradiating unit 111 becomes closer to the horizontal direction as it comes closer to the groove cams as shown in FIG. 5A and FIG. 5B.

The extension arms 156, 157 are connected via joints 158, 159 to the arms 116, 117 respectively with pivot-like mechanisms. Therefore, the arms 116, 117 are allowed to move either upward or downward in the drawing. As shown in FIGS. 5A and 5B, the extension arms 156, 157 are provided with adjusters 160, 161 for adjusting their lengths.

Figure 7:
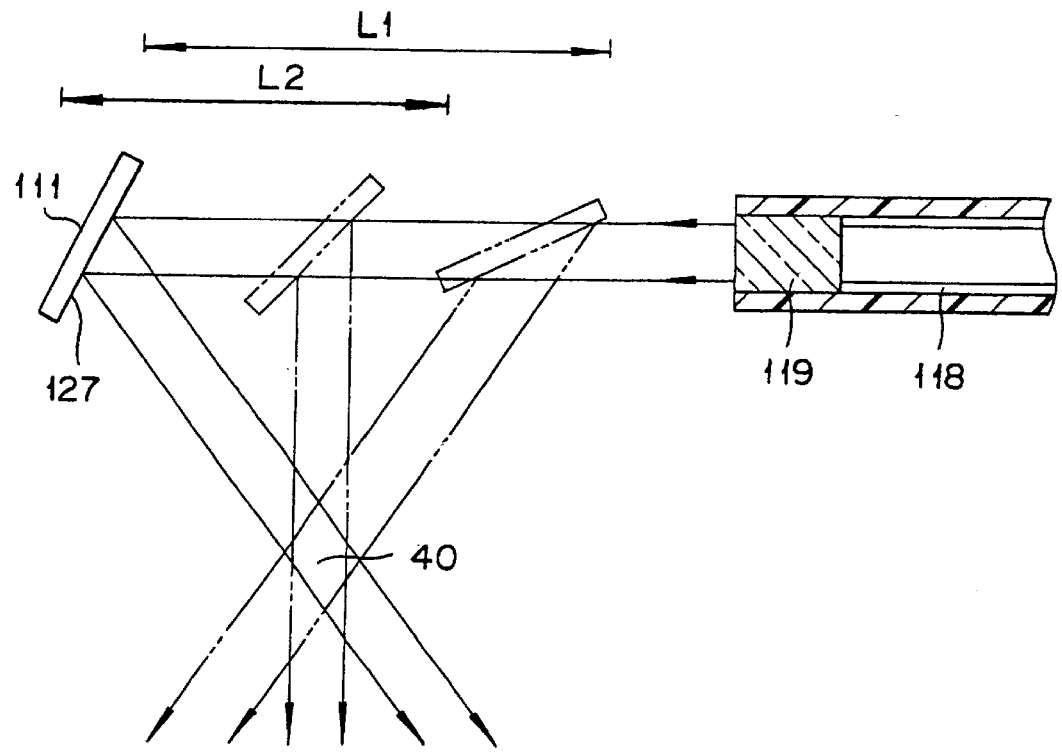
FIG. 7 is a drawing to describe the relation between the motion of the irradiating unit and the direction of the energy irradiation direction.

With such a constitution, the linear motion range L1 of the connecting part 128 of the irradiating unit 111 is longer than the linear motion range L2 of the connecting part 129, the tilt angle of the irradiating unit 111 varies with its position as shown in FIG. 7. In other words, as the irradiating unit 111 moves closer to the proximal end or the driving unit 150, the tilt angle of the irradiating unit 111 reduces, while the tilt angle of the irradiating unit 111 increases as the irradiating unit moves closer to the distal end. Therefore, the irradiating unit 111 always irradiates a target point 40 with the laser ray introduced by the optical fiber 118 regardless of the location of the irradiating unit 111. The linear motion range of the irradiating unit 111 can be adjusted by changing the lengths of the extension arms 156, 157 with the help of the adjusters 160, 161. Moreover, the angle range of the irradiating unit 111 is adjustable by changing the relative lengths of the extension arms 156, 157.

Figure 8:
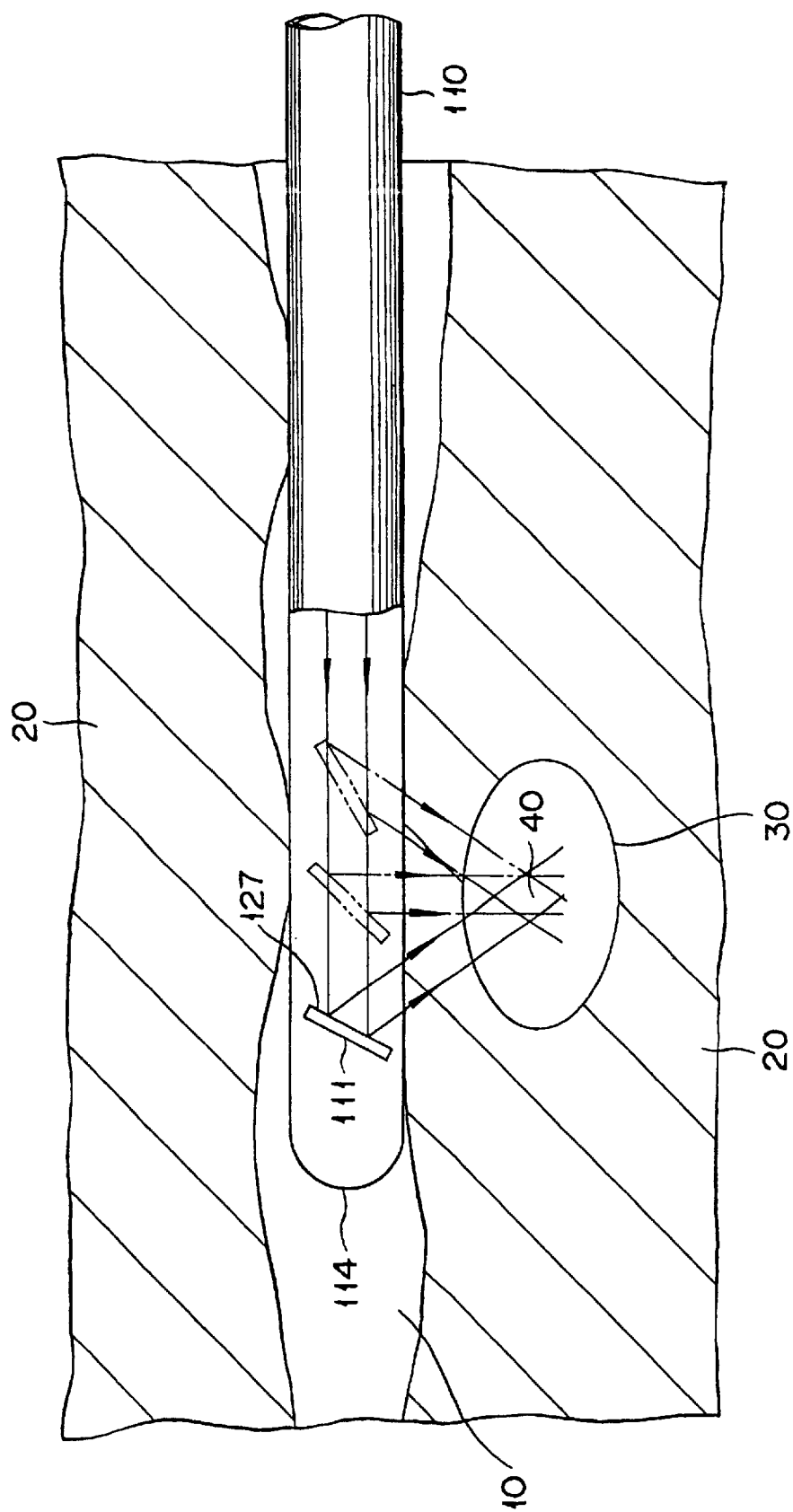
FIG. 8 is a cross section to describe an application of the laser ray irradiation apparatus.

Next, specific application condition and operation of the apparatus 100 will be described referring to FIG. 8.

First, the distal end of the body 110 is inserted into a celom 10, wherein the housing 112 that contains the irradiating unit 11 is made to contact with the surface layer of the proximity of a lesional region, i.e., a target region 30. At this time, it is preferable that the location of the housing 112 is confirmed directly using the endoscope 180.

It is preferable to adjust the lengths of the extension arms 156, 157 confirming the target point is located properly based on ultrasonic images or nuclear magnetic resonance images prior to the insertion of the apparatus 100 into the celom 10. The lengths of the extension arms 156, 157 are adjusted using the adjusters 160, 161 as described below so that the cross point of the laser ray, i.e., the target point 40 is located at a desired position within the target region 30.

In order to move the location of the target point 40 perpendicular to the axis of the body 110, engaging position of the extension arm 156 is changed as to the grooves 154A, 154B, 154C formed on the groove cam 151. Specifically, if the target point 40 is to be moved downward in FIG. 8 away from the housing 112, the groove inside the groove currently engaged with the extension arm 156, e.g. the groove 154C is to be used. Reciprocally, if the target point 40 is desired to be moved upward in FIG. 8 toward the housing 112, the groove outside the groove presently engaged with the extension arm 156, e.g. the groove 154A is to be used.

If the target point 40 is to be moved in the longitudinal direction of the body 110, the entire apparatus 100 is moved in the longitudinal direction of the body 110. However, the target point 40 can be likewise moved in the longitudinal direction of the body 110 by using the adjusters 160, 161. This is suitable for a case where the movement of the entire apparatus 100 is difficult for some reason. Specifically, if the target point 40 is to be moved toward the distal end, either the extension arm 156 is shortened by means of the adjuster 160, or the extension arm 157 is elongated by means of the adjuster 161. Reciprocally, if the target point 40 is desired to be moved toward the proximal end, either the extension arm 156 is elongated by means of the adjuster 160, or the extension arm 157 is shortened by means of the adjuster 161. If it is desired to move the target point 40 in the circumferential direction of the body 110, the entire apparatus 100 is rotated manually.

The adjustment of the position of the target point 40 is conducted as needed according to the methods described above in the direction perpendicular to the axis of the body 110, the longitudinal direction of the body 110, or in the circumferential direction of the body 110.

Next, the laser ray generating apparatus 120 and the motor 188 are activated simultaneously. The laser ray generated is then introduced into the optical fiber 118.

The optical fiber 118 is inserted into the apparatus 100 via the shock absorbing device 181. The laser ray is converted into a collimated ray by means of the lens 119 provided at the distal end of the optical fiber 118. After passing the lens 119, the laser ray is reflected off from the reflecting surface 127 of the irradiating unit 111 contained in the housing 112, and radiated on the target point 40. The irradiating unit 111 is reciprocated axially at frequencies of 0.1 Hz to 5 Hz, or more preferably 1 Hz to 3 Hz while changing the irradiation angle. While the path of the laser ray is constantly changing, it always passes through the target point 40.

As a result, the target point 40 and its proximity inside the tissue 20 become heated and reach a desired temperature. On the other hand, laser ray irradiation in any region above the target area 30 on the upper side of FIG. 8, for example, the surface layer of the tissue 20, is short so that the amount of heat generated is limited. Similarly, the laser ray irradiation in any region below the target area 30 on the lower side of FIG. 8 is also short so that the amount of heat generated is also limited. Therefore, the surrounding areas of the target area 30 are kept at relatively low temperatures to be protected from the effects of the laser ray. As the areas other than the target area 30 are protected from or have least chance of being damaged, the apparatus 100 has a highly safe characteristic for the patient. It is particularly beneficial in case when the target area 30 is located deep in the tissue as the surface layer is protected from being damaged.

Next, the position of the target point 40 is changed to initiate another round of irradiation. Repeating the above sequence, the entire target area 30 is heated and reaches the desired temperature.

As described in the above, the apparatus can move the target point 40 in any direction, particularly directions perpendicular to the axis of the body 110. Therefore, a uniform heating and a desired temperature can be easily achieved regardless of the position, shape or dimension of the target area 30. Also, localized excessive heating or insufficient heating can be prevented as well.

The laser ray radiated from the irradiating unit 111 is preferably collimated or convergent ray. However, divergent ray is also applicable for the purpose.

If the laser ray radiated from the irradiating unit 111 is collimated or convergent, the energy density at the target point 40 and its proximity can be enhanced because of its good convergence. In other words, if the energy density of the convergent or collimated laser ray and the energy density of the divergent laser ray are equal at the target point 40, the energy density in the surface layer is lower in the former than in the latter. Therefore, the collimated or convergent laser ray can more securely prevent damages in the surface layer than in the case of the divergent laser ray.

If the laser ray radiated from the irradiating unit 111 is convergent, it is preferable to be constituted in such a way that the target point 40 matches with the focus point of the laser ray, i.e., the point where the cross sectional area of the laser ray perpendicular to the axis of the laser ray becomes minimum. Since the focus point of the laser ray coincides with the target point 40, the energy density of the laser ray can be further intensified at the target point 40 and its proximity.

In order to make the laser ray radiated from the irradiating unit 111 convergent, an optical system is provided in the path of the laser ray. The apparatus 100 has a lens 119 located at the distal end of the optical fiber 118. It is also possible to arrange the irradiating unit 111 to function as an optical system by forming the reflecting surface 127 of the irradiating unit 111 as a concave mirror.

The cross sections of the working lumens 121, 122 of the body 110 can be arbitrary selected. For example, rectangular shapes can be used as well to accommodate the changes in the vertical position of the arms 116, 117 interlocked with the tilting angle of the irradiating unit 111.

Any kind of laser ray that has a capability of transmitting deep into the tissue can be used for the purpose of this invention. It is preferable, however, that the wavelength of the laser ray is in the ranges of 750 nm to 1300 nm or 1600 nm to 1800 nm, as laser rays in those wavelength ranges indicate excellent tissue transmitting capabilities. In other words, as the surface layer of a tissue absorbs only a small fraction of the energy radiated in those cases, the laser ray is radiated more effectively on the target area 30 located deep in the tissue.

For example, gaseous lasers such as He-Ne laser, solid lasers such as Nd-YAG, and semiconductor lasers such as GaAlAs are applicable for the laser ray generating apparatus to generate laser rays of said wavelength ranges.

There is no restriction as to the insertion part diameter of the apparatus 100, or the outer diameter of the body 110 as long as it can be inserted into the target celom. However, the outer diameter of the body 110 should be preferably 2 mm to 20 mm, or more preferably 3 mm to 8 mm.

The body 110 can be made of a polymer alloy containing either of polyolef in such as polyethylene and polypropylene, ethylene-vinylacetate copolymer (EVA), polyvinyl chloride, polyester such as polyethylene terephthalate and polybutylene terephthalate, polyamide, polyurethane, polystyrene, or fluorocarbon resin, or a combination thereof.

The surface of the body 110 can be covered with a lubricating coated layer containing a material with low friction characteristic such as silicone and fluorocarbon resin, or a hydrophilic polymer material. As such a coating reduces surface friction, it helps smooth insertion of the body 110 into the celom. As an alternative, a lubricating coated layer can be formed on the surface of a separately prepared perishable sheath covering the body 110. Such an arrangement can prevent the drawback of the lubricating coating layer being peeled off due to the repeated usage.

A hydrophilic polymer material used as the lubricating coated layer is preferably either carboxymethyl cellulose, polysaccharides, polyvinyl alcohol, polyethylene oxide, sodium polyacrylate, methyl vinyl ether-maleic anhydride copolymer, or water soluble polyamide, and more preferably methyl vinyl ether-maleic anhydride copolymer.

When a laser ray irradiation apparatus having a body coated with hydrophilic polymer is used, it is immersed in physiological saline as a preparation. This process provides wetness on the surface of the body and lubricity on the apparatus. In other words, the friction resistance between the tissue and the apparatus reduces if the surface layer of the body of the apparatus contains a hydrophilic polymer material. This alleviates the stress of the patient and improves safety. For example, insertion and extraction of the apparatus in and out of the celom, and the movement and rotation of the apparatus within the celom can be conducted smoothly without fail.

The housing 112 is preferably made of a material with an excellent laser ray transmission capability such as quartz glass, acrylic, polystyrene, polycarbonate, polyethylene, polypropylene, vinylidene chloride, and polyester. There is no need to form the housing 112 in its entirety out of a material with a laser ray transmission capability, so that only the window 115 can be made of such a material. Having the window 115 for laser ray irradiation made of a material with a good laser ray transmission capability assures an effective irradiation of the laser ray. It is also possible to form the window 115 with an opening and the covering member 113 that covers the housing 112 with one of the above-mentioned materials.

The energy transmitting material does not have to be an optical fiber, but any other member that is suitable for transmitting the laser ray, such as a rod lens. The irradiating unit does not have to be plate with a flat reflecting surface, but can also be a prism or wedge plate.

Embodiment 2

Figure 9:
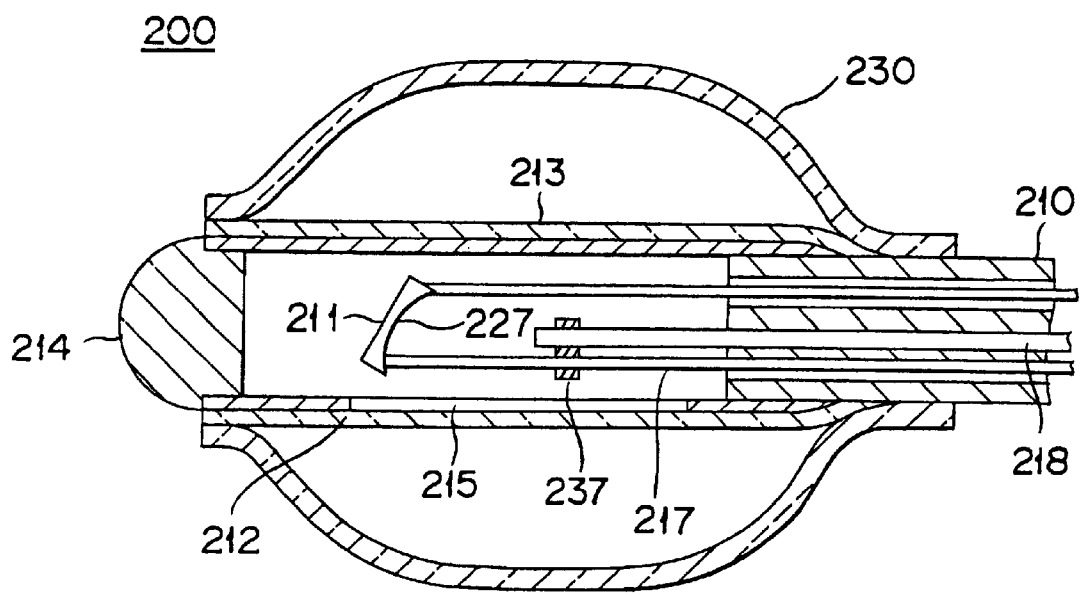
FIG. 9 is a cross section of a distal end of a laser ray irradiation apparatus of a second embodiment of the present invention.

An energy irradiation apparatus 200 shown in FIG. 9 is a lateral irradiating type laser ray irradiation apparatus similar to the Embodiment 1. Only the differences from the Embodiment 1 will be discussed in the following, skipping points of similarities.

The laser ray irradiation apparatus 200 includes an irradiating unit 211, which has a concave surface for reflecting and converging the laser ray transmitted by the optical fiber 218. Therefore, the apparatus 200 lacks the lens 119 of the apparatus 100 in the Embodiment 1 provided at the distal end of the optical fiber to converge the laser ray into a collimated ray. The optical fiber 218 and an arm 217 are fixed by a connector 237. Therefore, the optical fiber 218 and the arm 217 reciprocate as one unit, so that the distal end of the optical fiber 218, from which the laser ray is radiated, always maintains a constant distance against the reflecting surface 227 and the laser ray shape is also maintained substantially constant. Since the reciprocating motion of the optical fiber 218 is absorbed into a loop within a shock absorbing device (refer to the shock absorbing device 181 of FIG. 1), the optical fiber 218 is in a state of rest in the proximal end side over the shock absorbing device.

The apparatus 200 further includes a balloon 230 that expands or contracts. The balloon 230 surrounds a housing 212 located at the distal end of a body 210. The balloon 230 is preferably made of a material with an excellent laser ray transmission capability such as polyolefin, polyester, polyamide, latex and cellulose, so that the temperature increase caused by energy absorbed by the balloon 230 is reduced when the laser ray passes through the balloon 230.

The working fluid that expands the balloon 230 is supplied by the lumens (equivalent to the lumens 124, 125 shown in FIG. 3 related to the Embodiment 1) used for feeding and discharging the coolant. One ends of the lumens are respectively connected to feeding and discharging tubes of a coolant circulating device via inlet and outlet connectors provided in the apparatus 200, while the other ends are communicating with the balloon 230.

The working fluid can be any fluid as long as it is capable of expanding or contracting the balloon 230, but the coolant is preferable. It is because that, if the coolant is used as the working fluid, it cools the surface layer of the tissue during laser irradiation and prevents damages on the surface layer more securely.

If the target area is in prostate, it is preferable to maintain the target area temperature to about 48° C. to 100° C. and the temperatures of normal tissues, or the areas above or below the target area, below 44° C. The apparatus 200 is capable of radiating the laser ray to satisfy such a condition.

The temperature of the coolant, or the working fluid is not limited as long as it is capable of cooling the surface layer of the tissue. It is preferable to be below 37° C., or more preferably to be 0° C. to 25° C., or most preferably 0° C. to 10° C. Physiological saline is preferably used as the working fluid because any internal leakage of such a working fluid causes least damage. If the working fluid is also a coolant, it is preferable to circulate the working fluid in order to increase the cooling efficiency. It is also preferable to circulate the working fluid during the period of pre-irradiation to the completion of the laser irradiation.

It is preferable to provide at the outlet connector a pressure regulator such as a pressure valve that opens to release the working fluid when the pressure exceeds a certain value. This makes it possible to inflate the balloon 230 at a fixed pressure regardless of the flow volume of the working fluid. Incidentally, a depth position of the target point can be adjusted by controlling an expansion ratio or an expansion diameter of the balloon 230. It is preferable to control the temperature and the flow volume of the working fluid in relation to the laser irradiation. overcooling or overheating of the surface layer can be prevented in this case.

It is preferable to provide a temperature sensor on the balloon 230 to detect the surface temperature of the tissue. This makes it possible to cool the working fluid efficiently to a necessary and sufficient degree as the information about the surface temperature of the tissue, or the temperature detected by the sensor can be used to control the cooling of the working fluid.

Figure 10:
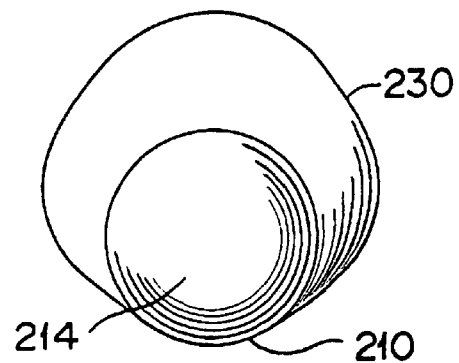
FIG. 10 is a front view of a modification according to the second embodiment.

The balloon 230 can be formed to surround the entire circumference of the housing 212 except the laser ray irradiation window 215 (see FIG. 9) of the body 210 as shown in FIG. 10. In this case, an excellent stability of the apparatus 200 is achieved during the laser ray irradiation period as the window 215 of the body 210 is pressed against the wall of the celom, or the surface of the tissue to stabilize the distance between the target area and the irradiating unit 211.

Next, the action of the apparatus 200 will be described.

With the balloon 230 being contracted, the distal end of the apparatus 200 is inserted into the celom to be located in lesional region, or in the proximity of the target area.

The coolant, or the working fluid, is fed into the balloon 230 by, for example, operating the pump connected to the inlet connector, and inflates the balloon 230 to a specified size. In more detail, the working fluid flows through the inlet connector and the feeding lumen into the cavity of the balloon 230 to inflate the balloon 230.

As the balloon 230 inflates, the position and direction of the apparatus 200 becomes fixed. This makes it possible to aim the laser ray irradiation at the target point within the target area more securely and easily. Moreover, the pressure genera ted due to the expansion of the balloon 230 is applied to the deep area of the tissue through the surface of the tissue. This causes shortening of the laser ray path from the irradiating unit 211 to the target point, which in turn causes reduction of energy loss, or energy absorption by the tissue so that it becomes possible to heat the target point to achieve a desired temperature with a lower energy level of the laser ray. Moreover, it becomes possible to prevent the damage of the surface layer more securely as the surface layer of the tissue, or the area that makes contact with the balloon 230 and its vicinity is cooled by the working fluid.

When the working fluid is circulated, the working fluid is fed from the inlet connector and discharged through the outlet connector. More specifically, the working fluid fed through the inlet connector flows into the balloon 230 via the feeding lumen. The working fluid circulates through the balloon 230 and is discharged through the outlet connector via the discharging lumen after circulating at least half way.

When the laser irradiation at the target area is completed, the flow of the working fluid through the inlet connector is stopped and only the discharge of the working fluid through the outlet connector is executed. As the working fluid in the balloon 230 is discharged through the outlet connector via the discharging lumen, the balloon 230 contracts. The body 210 is removed from the celom while the balloon is contracted.

The position and direction of the apparatus 200 is fixed more easily and securely as mentioned before by means of the balloon 230. Moreover, in the apparatus 200, the surface layer of the tissue is cooled with the working fluid in the balloon 230.

It is also possible to form a lubricating coated layer on the surface of the balloon 230 as in the Embodiment 1. It is also possible to provide a balloon in case of the laser ray irradiation apparatus 100 of the Embodiment 1.

Embodiment 3

Figure 11:
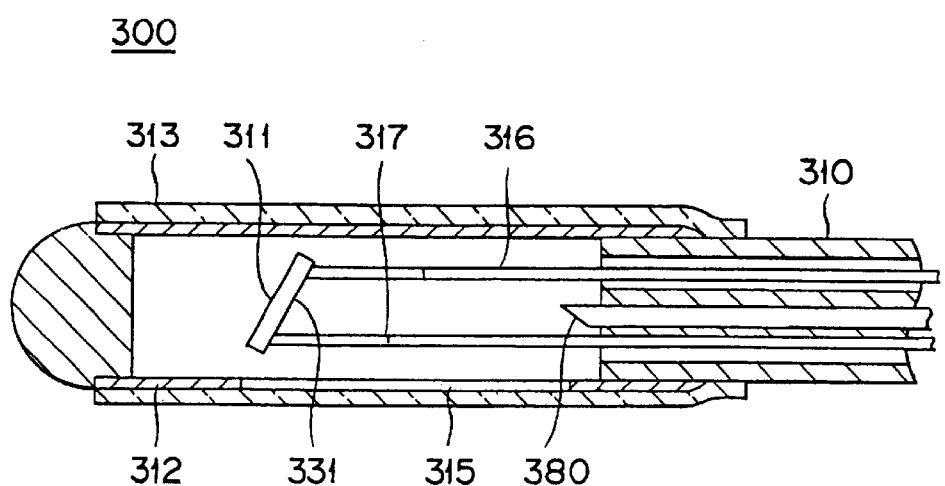
FIG. 11 is a cross section of a distal end of an ultrasonic irradiation apparatus of a third embodiment of the present invention.

An energy irradiation apparatus 300 shown in FIG. 11 is a lateral irradiating type ultrasonic ray irradiation apparatus typically used for the treatment of Benign Prostatic Hyperplasia and various tumor such as cancer by applying an ultrasonic ray into a tissue. Only the differences from the Embodiment 1 will be discussed in the following, skipping points of similarities.

The ultrasonic ray irradiation apparatus 300 includes a body 310 of a long shape, an irradiating unit 311 having an oscillator 331, which is an ultrasonic transducer that converts electric energy into ultrasonic ray, arms 316 and 317 that support the oscillator 331, and an endoscope 380.

The arms 316, 317 reciprocate the oscillator 331 in the axial direction of the body 310 as in the Embodiment 1. The arms 316 and 317 have clad structure composed of a conductor and an insulation coating layer serving as a lead wire to connect the oscillator 331 with the power source. More specifically, the power is supplied to the oscillator 331 via sliding contacts provided at groove cams (refer to the groove cams 154, 155 shown in FIG. 6). The conductors of the arms 316, 317 are electrically insulated from the groove cams.

A frequency of the ultrasonic ray cannot be determined indiscriminately as it varies with the type of organ where the lesional region exists, the location, depth and range of the lesional region. However, it is preferable to use the ultrasonic ray having the frequency in the range of 1 MHz to 50 MHz for the soft tissue located about 1 cm to 5 cm below the surface layer of the tissue.

The endoscope 380 is of an oblique viewing type using a optical fiber, is detachable from the apparatus 300, and is inserted from the proximal end of the apparatus 300. The optical fiber is capable of radiating the illumination light. Therefore, it is possible to observe the position irradiated by the ultrasonic ray, the irradiating direction and the irradiated surface condition by means of the endoscope 380. In other words, irradiation to improper areas can be prevented as the target area position can be confirmed accurately by means of the endoscope 380. Moreover, the irradiation condition can be arbitrarily changed as the irradiated surface condition can be observed continuously during the irradiation of the ultrasonic ray.

Embodiment 4

Figure 12:
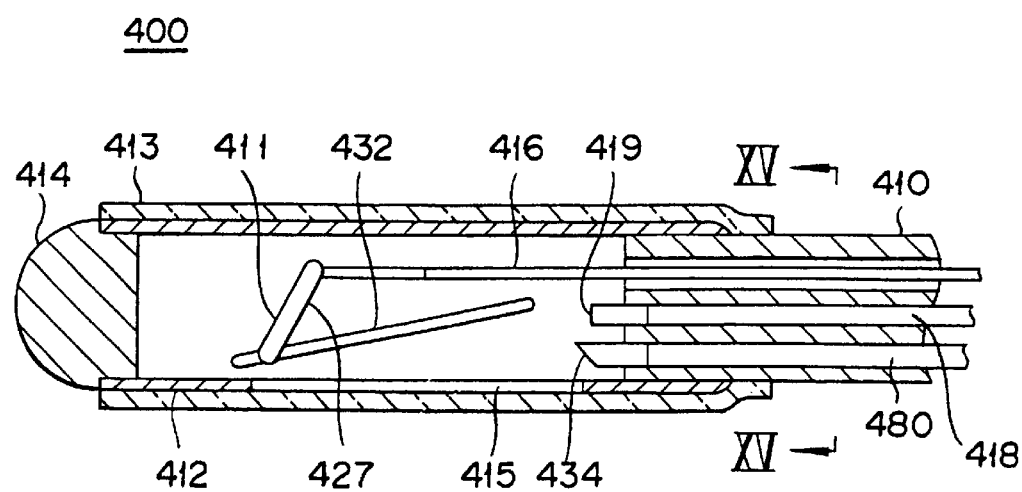
FIG. 12 is a cross section of a distal end of a laser ray irradiation apparatus of a fourth embodiment of the present invention.

An energy irradiation apparatus 400 shown in FIG. 12 is a lateral irradiating type laser ray irradiation apparatus typically used for the treatment of Benign Prostatic Hyperplasia and various tumor such as cancer by applying a laser ray capable of reaching deep into a tissue. Since its overall constitution is similar to the Embodiment 1, it description is omitted (refer to FIG. 1).

The laser ray irradiation apparatus 400 includes a body 410 having a long shape, an irradiating unit 411 that radiates laser ray, and a housing 412 that contains the irradiating unit 411 and is connected the distal end of the body 410. The irradiating unit 411 has a single arm 416. The arm 416 supports the irradiating unit 411 within the housing 412 in such a way as to be able to slide freely, and function as the transportation means for transporting it in the axial direction of the body 410. The irradiating unit 411 has a flat reflecting surface 427 formed on one side thereof to reflect the laser ray.

The housing 412 consists of a hard tubular body having a window 415 for radiating the laser ray and is covered with a laser ray transmitting cover member 413. The inner wall of the housing 412 has a pair of grooves 432 formed to be used for changing the irradiating angle of the irradiating unit 411. The two groves 432 that serve as a guide for the irradiating unit 411 are located facing each other across the irradiating unit 411 and are formed non-parallel to the axial direction of the body 410, i.e., tilted against the axial direction of the body 410. The distal end of the housing 412 is sealed by a cap 414.

An optical fiber (energy transmitting member) 418 is provided inside the body 410. A lens 419 is provided at the distal end of the optical fiber 418. The lens 419 is an optical element for converging laser ray into collimated ray. The optical fiber 418 passes through a shock absorbing device (refer to the shock absorbing device 181 of FIG., 1) to be connected to a laser ray generating apparatus, which generates laser ray, via a connector. The shock absorbing device that contains the optical fiber 418 forming a loop absorbs the motion and/or a load of the optical fiber 418.

The apparatus 400 further includes a removable endoscope 480. The endoscope 480 is inserted from the proximal end toward the distal end of the apparatus 400. A guide light for observation by the endoscope 480 is generated by another light source such as He-Ne laser, with which the laser ray generating apparatus is equipped, and is transmitted through the optical fiber 418. Therefore, it allows the operator to observe the surface layer of the position where it is irradiated with the laser ray, to position the housing properly based on the observation of the endoscope, and visual confirmation of the laser irradiation position. Since the irradiated surface can be continuously observed during a laser irradiation operation, the irradiation condition can be easily optimized based on the actual condition.

Figure 13:
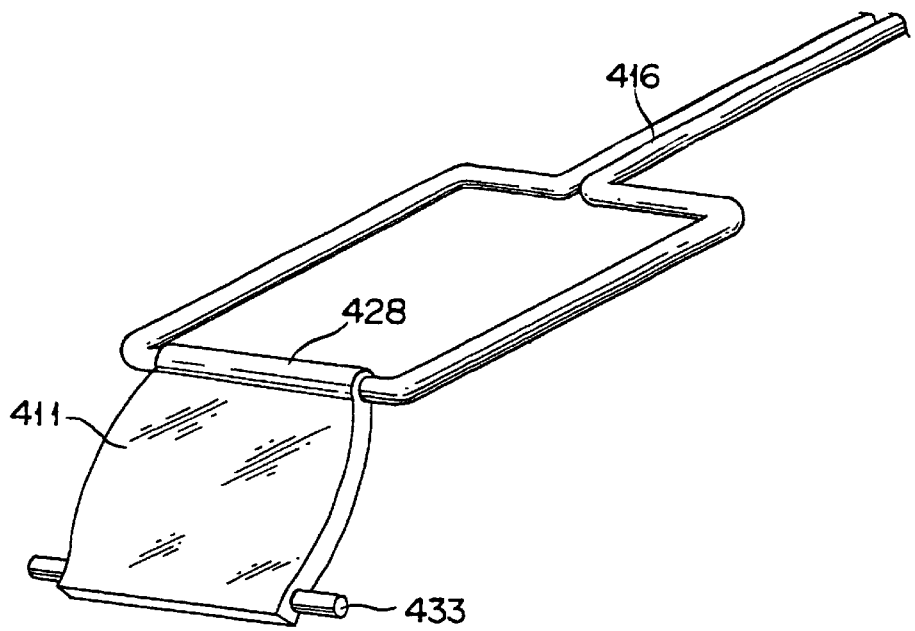
FIG. 13 is a perspective view for describing the structures of an irradiating unit and an arm of the laser ray irradiation apparatus.
Figure 14:
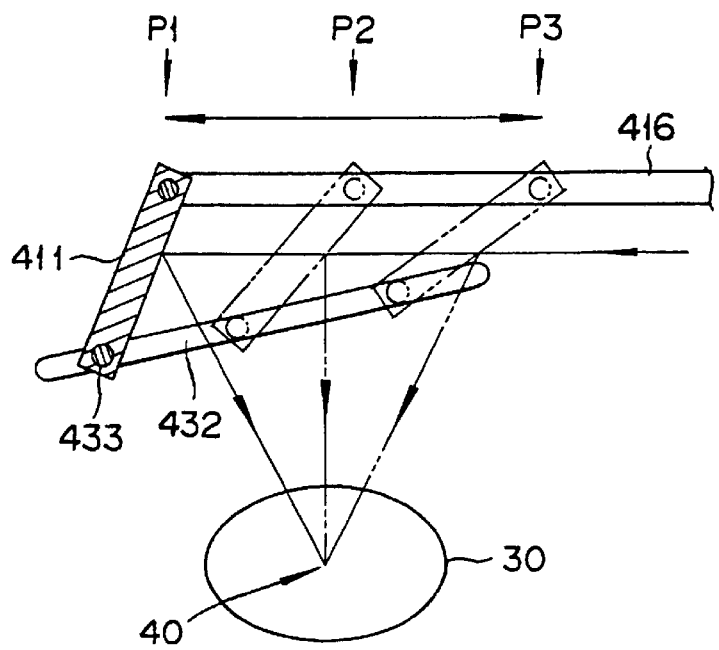
FIG. 14 is a drawing to describe the relation between the motion of the irradiating unit and the direction of the energy irradiation direction.

Next, the structures of the irradiating unit 411 and the arm 416 will be described referencing FIG. 13.

Since the arm 416 forks into the left and right side within the housing 412 to support the irradiating unit 411, it does not prevent the laser ray from irradiating the surface of the irradiating unit 411. The irradiating unit 411 is provided at one end thereof with a support part 428 and a pair of protrusions 433 on the other end. The support part 428 is provided rotatably on the arm 416 to accommodate changes of the irradiating angle of the irradiating unit 411. The protrusions 433 engage with the grooves 432 provided on the inner wall of the housing 412. The arm 416 is connected to the drive unit located at the apparatus base and is connected to a motor (electrical drive device). The drive unit reciprocates the irradiating unit 411 in the axial direction of the body. Therefore, the irradiating unit 411 changes its tilt angle as it moves its axial position on account of the interlocking action of the arm 416 and the grooves 432.

Next, the tilting angle change of the irradiating unit 411 will be described referring to FIG . 14.

The distance between the arm 416 and the non-parallel grove 432 at the point P2 is shorter than that at the position P1. Therefore, while the supporting par t 428 of the irradiating unit 411 travels from the position P1 to the position P2, the protrusions 433 of the irradiating unit 411 slide along the grooves 432 and the tilting angle of the irradiating unit 411 changes. In other words, the tilting angle of the irradiating unit 411 relative to the axis of the body reduces. Similarly, when the supporting part 428 of the irradiating unit 411 travels from the position P2 to the position P3, the tilting angle of the irradiating unit 411 further reduces. In the meantime, the laser ray reflected off from the irradiating unit 411 converges at the positions P1 through P3 on the target point 40 in the lesional region, or the target area 30.

In short, the laser ray continuously irradiates only the target point 40, so that other areas of the tissue such as the surface layer are irradiated only intermittently. As a result, the target point 40 is heated by the laser ray and reaches the desired temperature. On the other hand, other areas of the tissue such as the surface layer are irradiated only for short periods and thus are heated very little. The apparatus 400 can be applied to various lesional regions with complex shapes by designing the relation between the arm 416, which is parallel to the axial direction of the body, and the non-parallel groves 432, or the shape of the grooves 432 appropriately. For example, the grooves 432 can be curvilinear as opposed to a straight line.

Figure 15:
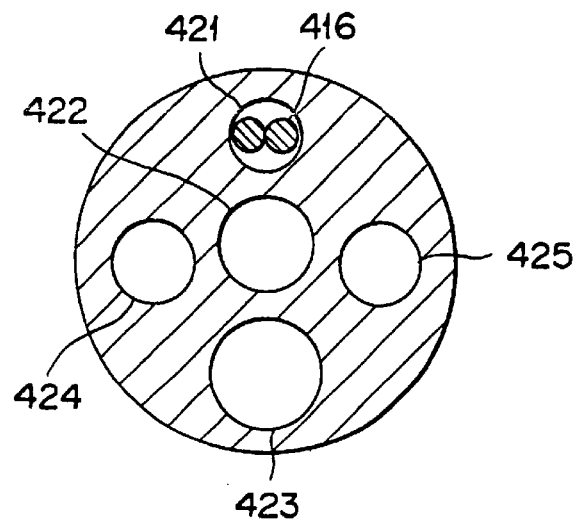
FIG. 15 is a cross section along the line XV—XV of FIG. 12.

As shown in FIG. 15, the body 410 of the apparatus 400 is equipped with a working lumen 421 into which the arm 416 can be inserted in such a way as to be able to slide freely. The working lumen 421 is provided in parallel with the axis of the body 410. The body 410 is further equipped with a lumen 422 for the optical fiber 418, a lumen 423 for the endoscope 480 as well as lumen 424, 425 for feeding and discharging the coolant. The coolant is used for alleviating the heat generated in the housing 412 due to the laser ray, and to cool the surface layer of the tissue that contacts with the housing 412. The lumens 424, 425 are respectively connected to feeding and discharging tubes (refer to the tubes 185, 86 of FIG. 1) of a coolant circulating device via an inlet connector and an outlet connector provided in the apparatus. In order to prevent the coolant from flow backward toward the proximal end, it is preferable that each of the lumens 421, 422, 423, and 426 has a check valve. It is possible to use the working lumens 421, 422 for coolant feeding and discharging as well. Physiological saline is used as a preferable coolant, because any leakage of such a coolant into a tissue causes least damage.

Figure 16:
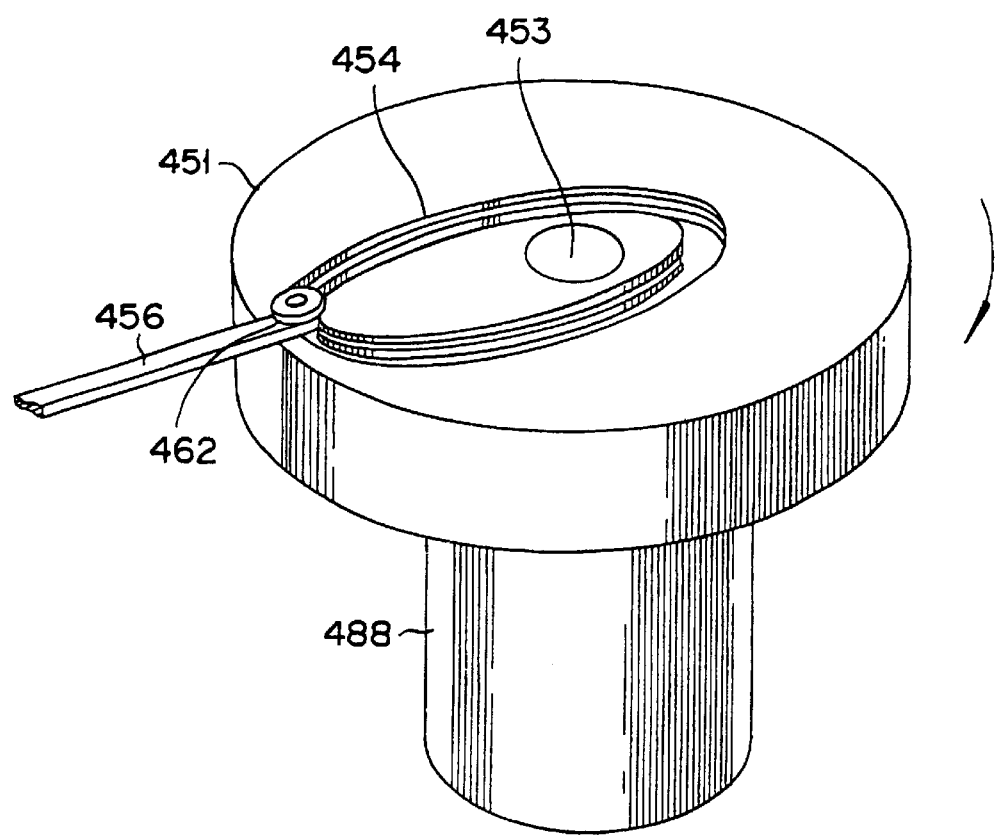
FIG. 16 is a perspective drawing for describing the structure of a drive unit of the laser ray irradiation apparatus.

The drive unit 450 used to reciprocate the irradiating unit 411 includes a groove cam 451 shown in FIG. 16. The groove cam 451 has an elliptical groove 454. A rotating shaft 453 of the groove cam 451 is connected to the shaft of a motor 488 and offset from the center of the groove 454. The drive unit 450 further includes a cam follower 462 provided at the proximal end of the rod 456 connected to the proximal end of the arm 416. The cam follower 462 engages with the groove 454 in such a manner as it can slide freely.

The groove cam 451 is driven by the motor 488 and is rotated around the rotating shaft 453. The cam follower 462 is not rotated but rather is caused to slide along the groove 454. Since the rotating shaft 453 is offset from the center of the groove 454, the rod 456 and the arm 416 connected to the rod 456 repeat reciprocating motions, or linear motions.

Next, the specific operating condition and action of the apparatus 400 will be described referring to FIG. 17.

First, the distal end of the body 410 is inserted into the celom 10, and the housing 412 that contains the irradiating unit 411 is caused to contact the surface layer in a proximity of the lesional region, or the target area. It is preferable that the location of the housing 412 is confirmed directly by means of the endoscope 480. The position of the target point 40 is adjusted by moving the entire apparatus 400 in the longitudinal direction of the body 410. The position of the target point 40 relative to the circumferential direction of the body 410 is adjusted by rotating the entire apparatus 400 manually.

Next, the laser ray generating apparatus and the motor 488 are activated simultaneously. The laser ray generated is then introduced into the optical fiber 418.

The optical fiber 418 is inserted into the apparatus 400 via the shock absorbing device. The laser ray is converted into a collimated ray by means of the lens 419 provided at the distal end of the optical fiber 418. After passing the lens 419, the laser ray is reflected off from the reflecting surface 427 of the irradiating unit 411 contained in the housing 412, and radiated on the target point 40. The irradiating unit 411 is reciprocated axially at frequencies of 0.1 Hz to 5 Hz, or more preferably 1 Hz to 3 Hz while changing the irradiation angle. While the path of the laser ray is constantly changing, it always passes through the target point 40.

As a result, the target point 40 and its proximity inside the tissue 20 become heated and reach a desired temperature. On the other hand, laser ray irradiation in any region above the target area 30 on the upper side of FIG. 17, for example, the surface layer of the tissue 20, is short so that the amount of heat generated is limited. Similarly, the laser ray irradiation in any region below the target area 30 on the lower side of FIG. 17 is also short so that the amount of heat generated is also limited. Therefore, the surrounding areas of the target area 30 are kept at relatively low temperatures to be protected from the effects of the laser ray. As the areas other than the target area 30 are protected from or have least chance of being damaged, the apparatus 400 has a highly safe characteristic for the patient. It is particularly beneficial in case when the target area 30 is located deep in the tissue as the surface layer is protected from being damaged.

Next, the position of the target point 40 is changed to initiate another round of irradiation. Repeating the above sequence, the entire target area 30 is heated and reaches the desired temperature.

As described in the above, the apparatus 400 can move the target point 40 in any direction, particularly directions perpendicular to the axis of the body 410 by moving the entire body 410 manually. Therefore, a uniform heating and a desired temperature can be easily achieved regardless of the position, shape or dimension of the target area 30. Also, localized excessive heating or insufficient heating can be prevented as well.

The laser ray radiated from the irradiating unit 411 is preferably collimated or convergent ray. However, divergent ray is also applicable for the purpose.

If the laser ray radiated from the irradiating unit 411 is collimated or convergent, the energy density at the target point 40 and its proximity can be enhanced because of its good convergence. In other words, if the energy density of the convergent or collimated laser ray and the energy density of the divergent laser ray are equal at the target point 40, the energy density in the surface layer is lower in the former than in the latter. Therefore, the collimated or convergent laser ray can more securely prevent damages in the surface layer than in the case of the divergent laser ray.

If the laser ray radiated from the irradiating unit 411 is convergent, it is preferable to be constituted in such a way that the target point 40 matches with the focus point of the laser ray, i.e., the point where the cross sectional area of the laser ray perpendicular to the axis of the laser ray becomes minimum. Since the focus point of the laser ray coincides with the target point 40, the energy density of the laser ray can be further intensified at the target point 40 and its proximity.

In order to make the laser ray radiated from the irradiating unit 411 convergent, an optical system is provided in the path of the laser ray. The apparatus 400 has a lens 419 located at the distal end of the optical fiber 418. It is also possible to arrange the irradiating unit 411 to function as an optical system by forming the reflecting surface 427 of the irradiating unit 411 as a concave mirror.

Any kind of laser ray that has a capability of transmitting deep into tissues can be used for the purpose of this invention. It is preferable, however, that the wavelength of the laser ray is in the ranges of 750 nm to 1300 nm or 1600 nm to 1800 nm, as laser rays in those wavelength ranges indicate excellent tissue transmitting capabilities. In other words, as the surface layer of a tissue absorbs only a small fraction of the energy radiated in those cases, the laser ray is radiated more effectively on the target area 30 located deep in the tissue.

For example, gaseous lasers such as He-Ne laser, solid lasers such as Nd-YAG, and semiconductor lasers such as GaAlAs are applicable for the laser ray generating apparatus to generate laser rays of said wavelength ranges.

There is no restriction as to the insertion part diameter of the apparatus 400, or the outer diameter of the body 410 as long as it can be inserted into the target celom. However, the outer diameter of the body 410 should be preferably 2 mm to 20 mm, or more preferably 3 mm to 8 mm.

The body 410 can be made of a polymer alloy containing either of polyolef in such as polyethylene and polypropylene, ethylene-vinylacetate copolymer (EVA), polyvinyl chloride, polyester such as polyethylene terephthalate and polybutylene terephthalate, polyamide, polyurethane, polystyrene, or fluorocarbon resin, or a combination thereof.

The surface of the body 410 can be covered with a lubricating coated layer containing a material with low friction characteristic such as silicone and fluorocarbon resin, or a hydrophilic polymer material. As such a coating reduces surface friction, it helps smooth insertion of the body 410 into the celom. As an alternative, a lubricating coated layer can be formed on the surface of a separately prepared perishable sheath covering the body 410. Such an arrangement can prevent the drawback of the lubricating coating layer being peeled off due to the repeated usage.

A hydrophilic polymer material used as the lubricating coated layer is preferably either carboxymethyl cellulose, polysaccharides, polyvinyl alcohol, polyethylene oxide, sodium polyacrylate, methyl vinyl ether-maleic anhydride copolymer, or water soluble polyamide, and more preferably methyl vinyl ether-maleic anhydride copolymer.

When a laser ray irradiation apparatus having a body coated with hydrophilic polymer is used, it is immersed in physiological saline as a preparation. This process provides wetness on the surface of the body and lubricity on the apparatus. In other words, the friction resistance between the tissue and the apparatus reduces if the surface layer of the body of the apparatus contains a hydrophilic polymer material. This alleviates the stress of the patient and improves safety. For example, insertion and extraction of the apparatus in and out of the celom, and the movement and rotation of the apparatus within the celom can be conducted smoothly without fail.

The housing 412 is preferably made of a material with an excellent laser ray transmission capability such as quartz glass, acrylic, polystyrene, polycarbonate, polyethylene, polypropylene, vinylidene chloride, and polyester. There is no need to form the housing 412 in its entirety out of a material with a laser ray transmission capability, so that only the window 415 can be made of such a material. Having the window 415 for laser ray irradiation made of a material with a good laser ray transmission capability assures an effective irradiation of the laser ray. It is also possible to form the window 415 with an opening and the covering member 413 that covers the housing 412 with one of the above-mentioned materials.

The energy transmitting material does not have to be an optical fiber, but any other member that is suitable for transmitting the laser ray, such as a rod lens. The irradiating unit does not have to be plate with a flat reflecting surface, but can also be a prism or wedge plate.

Embodiment 5

Figure 18:
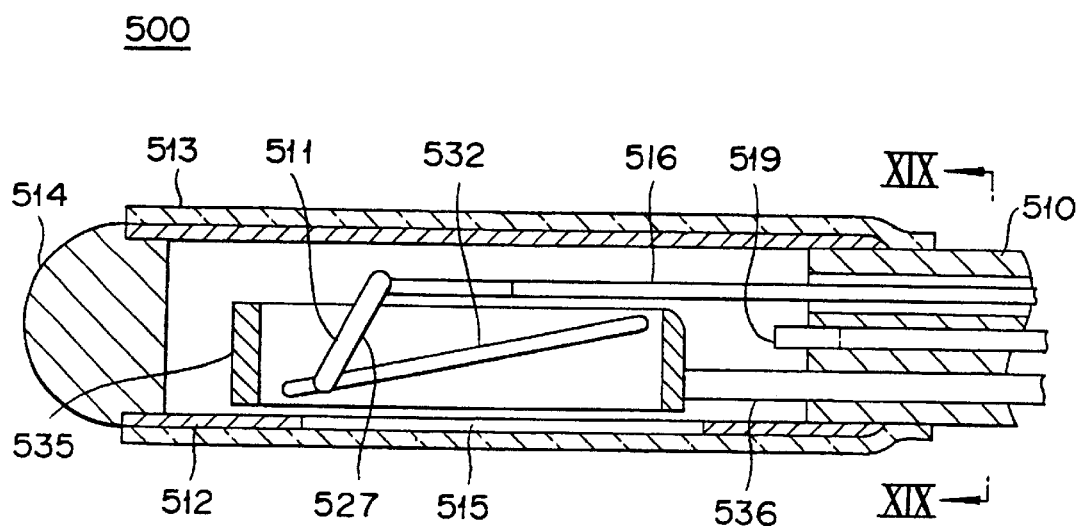
FIG. 18 is a cross section of a distal end of a laser ray irradiation apparatus of a fifth embodiment of the present invention.

An energy irradiation apparatus 500 shown in FIG. 18 is a lateral irradiating type irradiation apparatus similar to the Embodiment 4. Only the differences from the Embodiment 4 will be discussed in the following, skipping points of similarities.

The laser ray irradiation apparatus 500 includes a rail member 535, and a positioning rod 536 that moves the rail member 535 in the axial direction of the body 510. The rail member 535 has a pair of grooves (guides) 532 that engages with a pair of protrusions (refer to the protrusions 433 of FIG. 13) provided on an irradiating unit 511.

When the rail member 535 moves toward the proximal end, the protrusions of the irradiating unit 511 slide along the grooves 532, the tilting angle of the irradiating unit 511 increases, and the target point, or the focus point of the laser ray moves toward the proximal end. As a result, a lesional region, or target area spreading in a wide range relative to the axial direction of the body 510 can be heated by simply moving the rail member 535, not the entire apparatus 500. This mechanism can reduce excoriation or abraded wound which may be caused by the movement of the apparatus 500.

The rail member 535 has a notched area that corresponds to the path of the laser ray so that it does not affect the passage of the laser ray. However, if the rail member 535 is made of a laser ray transmitting material such as acrylic resin and quartz, the notching is not necessary as the laser ray passes through the rail member 535.

Figure 19:
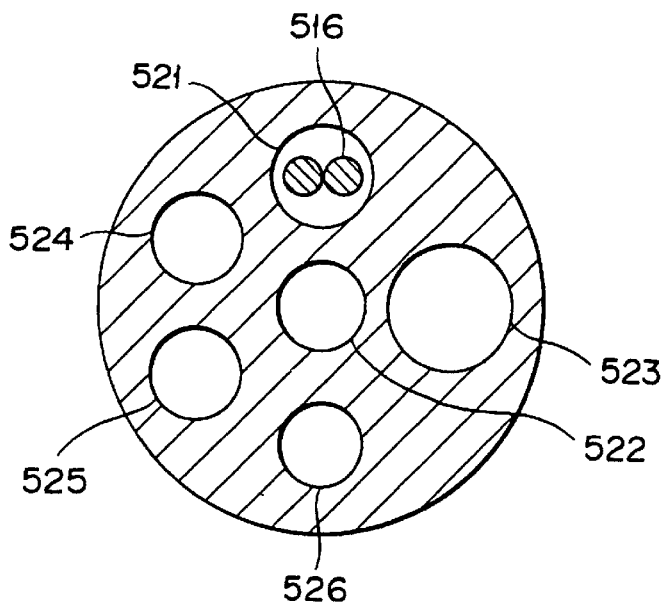
FIG. 19 is a cross section along the line XIX—XIX of FIG. 18.

In comparison with FIG. 15 of the Embodiment 4, the body 510 is added with a lumen 526 for accommodating a positioning rod 536 and the overall lumen arrangement is changed accordingly as shown in FIG. 19.

Figure 20:
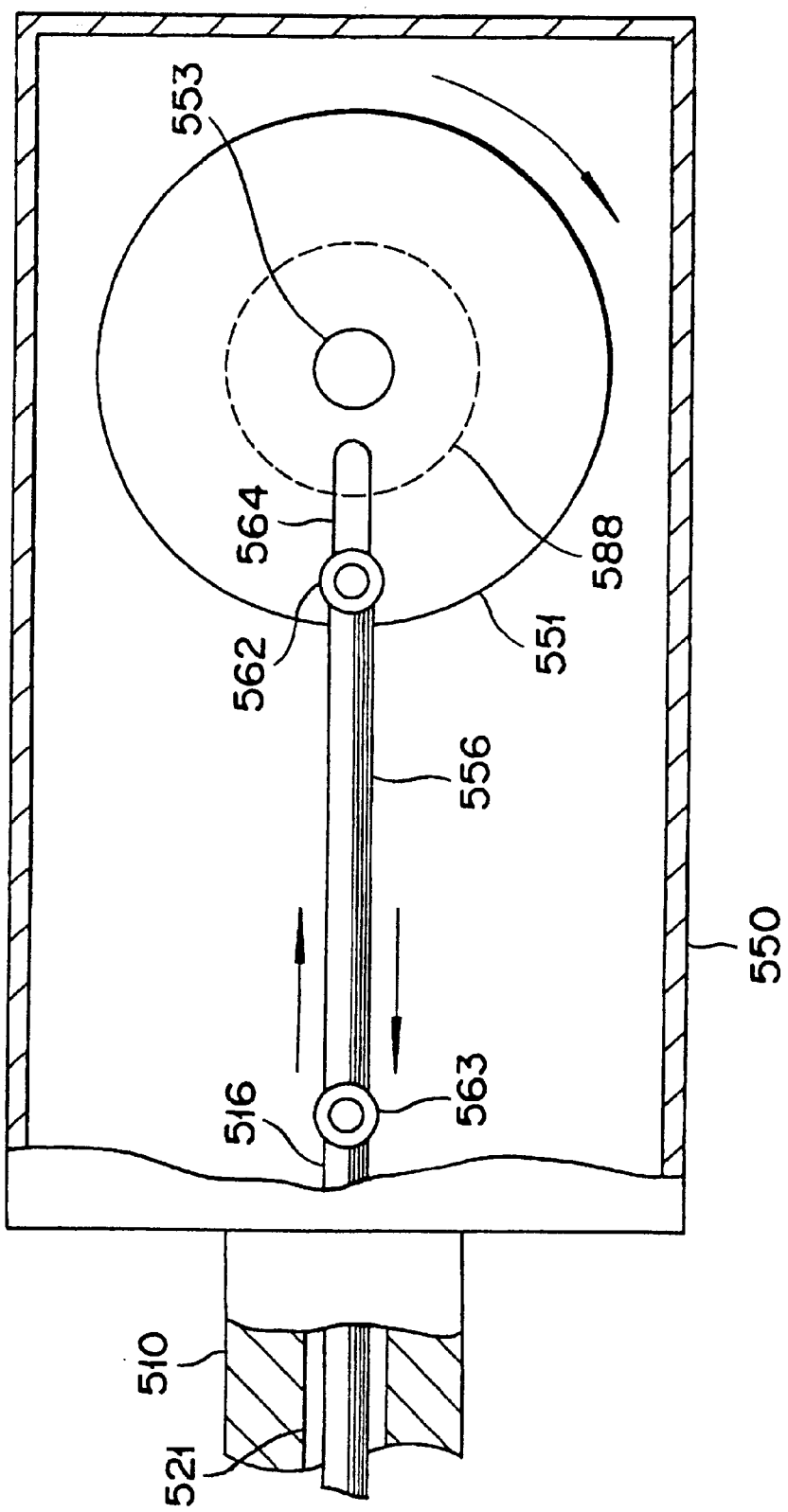
FIG. 20 is a drawing for describing the structure of a drive unit of the laser ray irradiation apparatus.
Figure 21A:
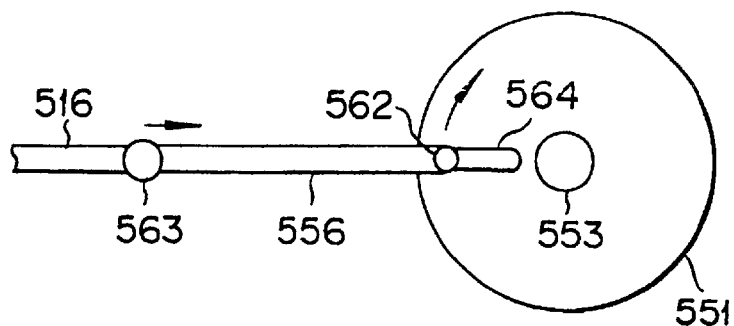
FIGS. 21A to 21D are drawings for describing the drive unit.
Figure 21B:
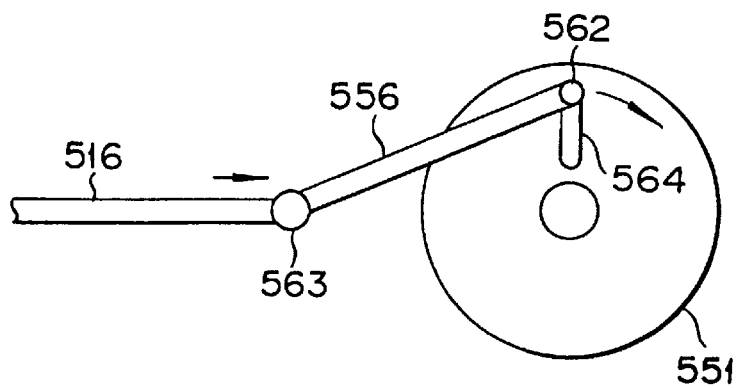
Figure 21C:
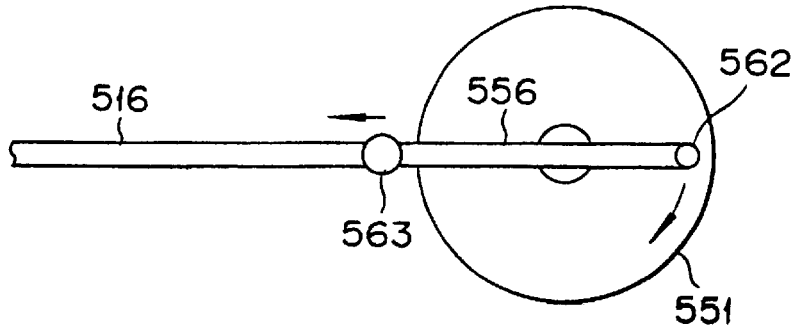
Figure 21D:
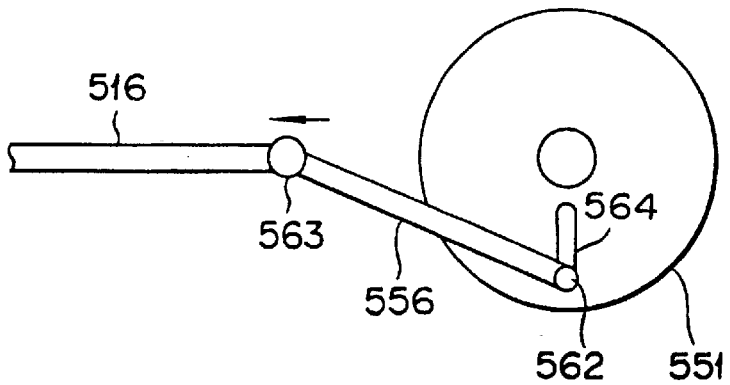

Next, the internal structure of the drive unit 550 of the apparatus 500 will be described referring to FIG. 20. In order to facilitate the understanding of the drive mechanism, lumens other than the working lumen 521, positioning rods, optical fiber, endoscope, etc. are not shown here, grossly simplifying the drawing.

The drive unit 550 is provided with a rotor 551. The rotor 551 includes a shaft 553, which is connected to the shaft of a motor 588, and a groove 564 formed in the radial direction on the surface. The rotor 551 is connected to one end of the rod 556 via a joint 562 having a screw member. The joint 562 is positioned along the groove 564 and is fixed to the rotor 551 by means of the screw member. The other end of the rod 556 is connected pivotally to one end of the arm 516 via the joint 563. The other end of the arm 516 is connected to the irradiating unit 511 via the working lumen 521 of the body 510. The reciprocating range of the irradiating unit 511 can be adjusted by changing the rotating radius of the joint 562 by moving the fixing position of the joint 562.

As described above, the alarm 516 is supported in the working lumen 521 of the body 510 of a long shape in such a way that it can slide freely. One end of the arm 516 is connected to the rod 556 pivotally via a joint 563, while the other end is connected to the irradiating unit 511. As a result, the arm 516 moves only in the axial direction of the body 510 and does not move in the vertical direction of the drawing as shown in FIG. 21A through FIG. 21D. The arm 516 and the irradiating unit 511 connected to the distal end of the arm 516 repeats a reciprocating motion between the position shown in FIG. 21A and the position shown in FIG. 21C. As a result, the reciprocating motion range of the irradiating unit 511 is twice the rotating radius of the joint 562.

Next, the specific operating condition and the action of the apparatus 500 will be described.

Figure 17:
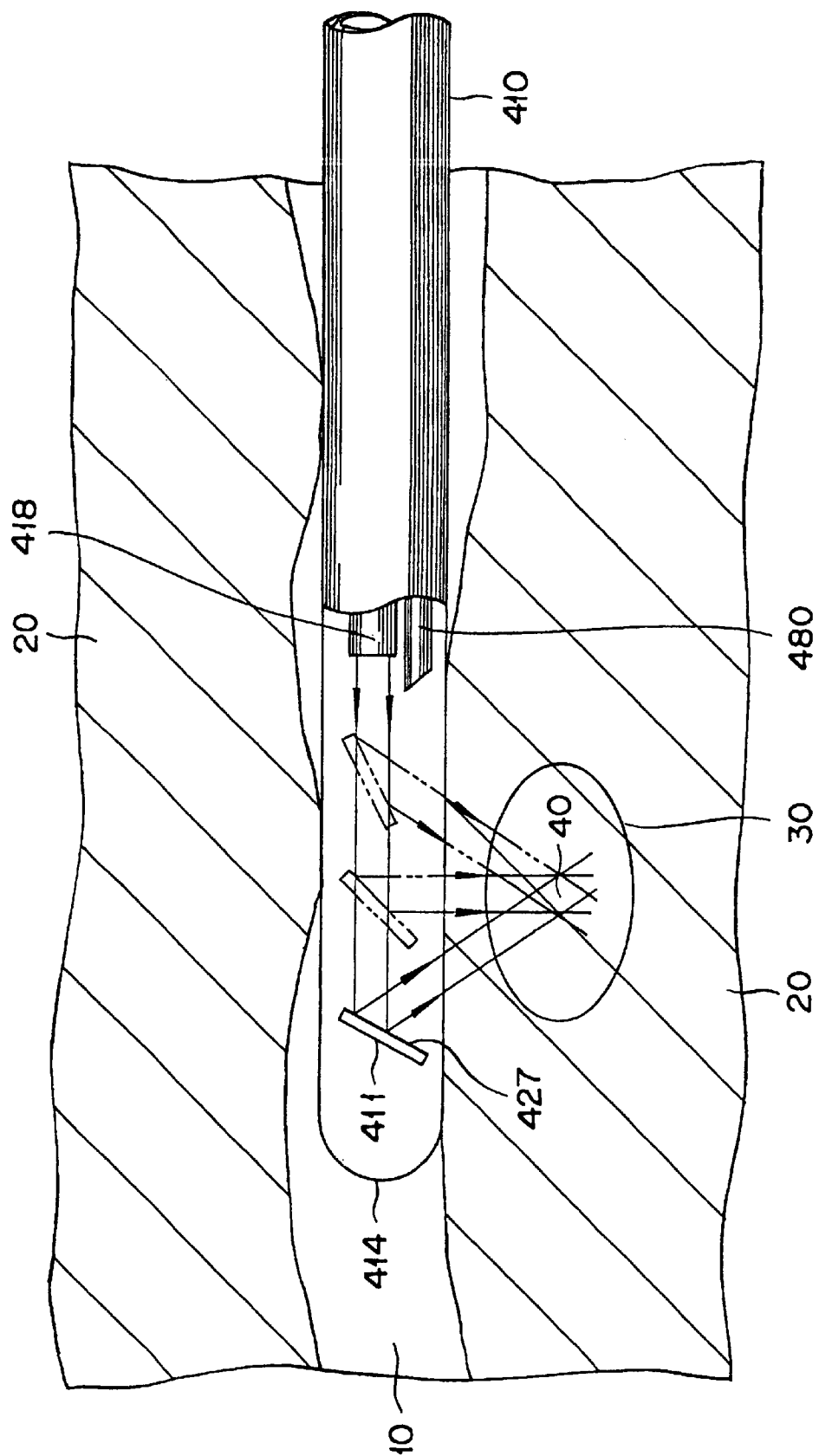
FIG. 17 is a cross section for describing an application of the laser ray irradiation apparatus.

First, similar to the Embodiment 4 shown in FIG. 17, the distal end of the body 510 is inserted into the celom 10, and the housing 512 that contains the irradiating unit 511 is caused to contact the surface layer in a proximity of the lesional region, or the target area 30. It is preferable that the location of the housing 512 is confirmed directly by means of the endoscope 580.

Next, the target point 40 is set at a desired location within the target area 30. The laser ray generating apparatus is turned on and the motor 588 is turned on simultaneously. The generated laser ray is then reflected off from the reflecting surface 527 of the reflecting unit 511, and radiated at the target point 40. In the meanwhile, the irradiating unit 511 is reciprocated in the axial direction by changing the irradiated angle. After completing the processing, the position of the target point 40 is changed and the laser ray is radiated. By repeating this cycle, the entire target area 30 can be heated and reach the desired temperature.

More specifically, the position of the positioning rod 536 is changed, and the position of the rail member 535 is adjusted. In addition, the joint 562 is fixed to the desired position of the groove 564. It is preferable that these settings are completed by confirming the target point based on ultrasonic images or nuclear magnetic resonance images prior to the insertion of the distal end of the body 510 into the celom 10.

When the rail member 535 is moved toward the distal direction, the target point 40 moves in the distal direction. When the joint 562 is moved toward the center of the rotor 551, the reciprocating motion range of the irradiating unit 511 becomes shorter and the target point 40 becomes closer to the surface layer, because the surface layer cooling effect deteriorates.

When the rail member 535 moves toward the proximal end, the target point 40 moves toward the proximal end. When the joint 562 is moved in a direction away from the center of the rotor 551, the reciprocating motion range of the irradiating unit 511 becomes longer, and the target point 40 moves toward the proximal end as well as toward the direction away from the surface layer, or toward the deeper area of the tissue.

The position of the target point 40 relative to the circumferential direction of the body 510 can be adjusted by manually turning the entire apparatus 500. Other actions are the same as the Embodiment 4.

Embodiment 6

Figure 22:
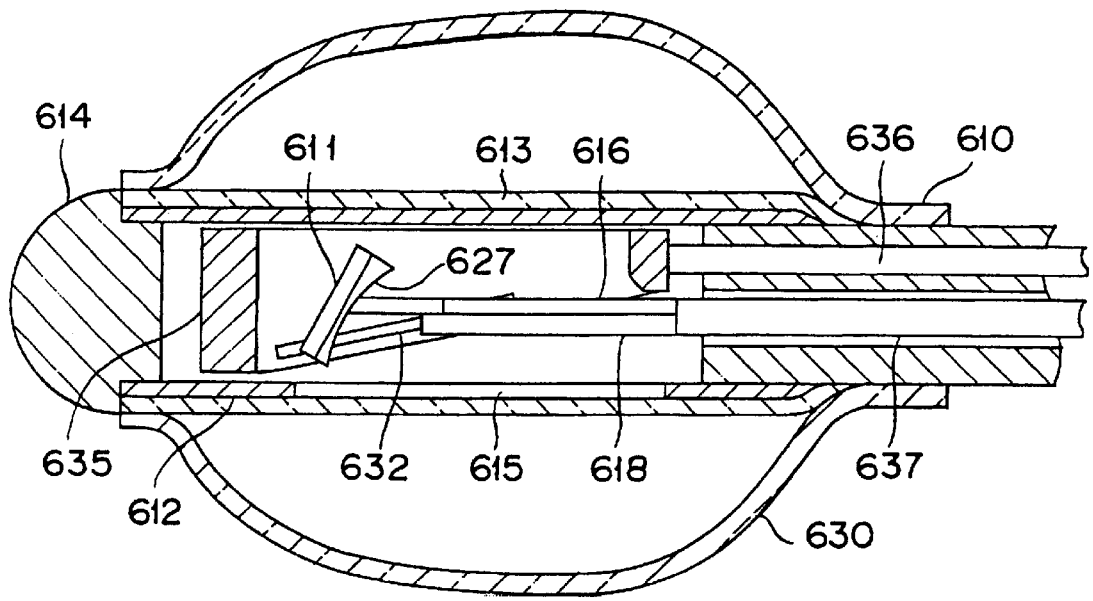
FIG. 22 is a cross section of a distal end of a laser ray irradiation apparatus of a sixth embodiment according to the present invention.

An energy irradiation apparatus 600 shown in FIG. 22 is lateral irradiating type irradiation apparatus similar to the Embodiment 4 and the Embodiment 5. only the differences from the Embodiment 4 and the Embodiment 5 will be discussed in the following, skipping points of similarities.

The laser ray irradiation apparatus 600 is equipped with an irradiating unit 611 having a reflecting surface 627 of a concave shape to reflect and converge the laser ray transmitted by an optical fiber 618. Therefore, the apparatus 600 is different from the Embodiment 4 and the Embodiment 5 in that it lacks lenses such as the lenses 419, 519 provided at the distal end of the optical fiber to converge the laser ray into a collimated ray. The optical fiber 618 and the arm 616 are inserted into the tube 637 and fixed to each other. Therefore, the optical fiber 618 and the arm 616 reciprocate as one unit, so that the distal end of the optical fiber 618, from which the laser ray is radiated, always maintains a constant distance against the reflecting surface 627 and the laser ray shape is also maintained substantially constant. Since the reciprocating motion of the optical fiber 618 is absorbed into a loop within a shock absorbing device (refer to the shock absorbing device 181 of FIG., 1), the optical fiber 618 is in a state of rest in the proximal end side over the shock absorbing device.

The apparatus 600 further includes a balloon 630 that expands or contracts. The balloon 630 surrounds a housing 612 located at the distal end of a body 610. The balloon 630 is preferably made of a material with an excellent laser ray transmission capability such as polyolef in, polyester, polyamide, latex and cellulose, so that the temperature increase caused by energy absorbed by the balloon 630 is reduced when the laser ray passes through the balloon 630.

The working fluid that expands the balloon 630 is supplied by the lumens (equivalent to the lumens 424, 425 shown in FIG. 15 related to the Embodiment 4) used for feeding and discharging the coolant. One ends of the lumens are respectively connected to feeding and discharging tubes of a coolant circulating device via inlet and outlet connectors provided in. the apparatus 600, while the other ends are communicating with the balloon 630.

The working fluid can be any fluid as long as it is capable of expanding or contracting the balloon 630, but the coolant is preferable. It is because that, if the coolant is used as the working fluid, it cools the surface layer of the tissue during laser irradiation and prevents damages on the surface layer more securely.

If the target area is in prostate, it is preferable to maintain the target area temperature to about 48° C. to 100° C. and the temperatures of normal tissues, or the areas above or below the target area, below 44° C. The apparatus 600 is capable of radiating the laser ray to satisfy such a condition.

The temperature of the coolant, or the working fluid is not limited as long as it is capable of cooling the surface layer of the tissue. It is preferable to be below 37° C., or more preferably to be 0° C. to 25° C., or most preferably 0° C. to 10° C. Physiological saline is preferably used as the working fluid because any internal leakage of such a working fluid causes least damage. If the working fluid is also a coolant, it is preferable to circulate the working fluid in order to increase the cooling efficiency. It is also preferable to circulate the working fluid during the period of pre-irradiation to the completion of the laser irradiation.

It is preferable to provide at the outlet connector a pressure regulator such as a pressure valve that opens to release the working fluid when the pressure exceeds a certain value. This makes it possible to inflate the balloon 630 at a fixed pressure regardless of the flow volume of the working fluid. Incidentally, a depth position of the target point can be adjusted by controlling an expansion ratio or an expansion diameter of the balloon 630. It is preferable to control the temperature and the flow volume of the working fluid in relation to the laser irradiation. Overcooling or overheating of the surface layer can be prevented in this case.

It is preferable to provide a temperature sensor on the balloon 630 to detect the surface temperature of the tissue. This makes it possible to cool the working fluid efficiently to a necessary and sufficient degree as the information about the surface temperature of the tissue, or the temperature detected by the sensor can be used to control the cooling of the working fluid.

Figure 23:
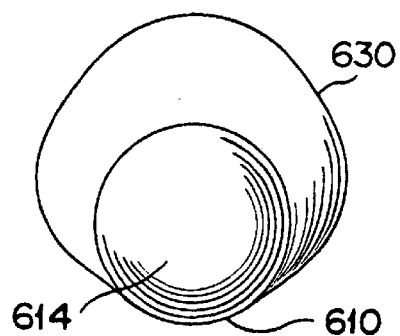
FIG. 23 is a font view of a modification according to the sixth embodiment of the present invention.

The balloon 630 can be formed to surround the entire circumference of the housing 612 except the laser ray irradiation window 615 (see FIG. 22) of the body 610 as shown in FIG. 23. In this case, an excellent stability of the apparatus 600 is achieved during the laser ray irradiation period as the window 615 of the body 610 is pressed against the wall of the celom, or the surface of the tissue to stabilize the distance between the target area and the irradiating unit 611.

Next, the action of the apparatus 600 will be described.

With the balloon 630 being contracted, the distal end of the apparatus 600 is inserted into the celom to be located in lesional region, or in the proximity of the target area.

The coolant, or the working fluid, is fed into the balloon 630 by, for example, operating the pump connected to the inlet connector, and inflates the balloon 630 to a specified size. In more detail, the working fluid flows through the inlet connector and the feeding lumen into the cavity of the balloon 630 to inflate the balloon 630.

As the balloon 630 inflates, the position and direction of the apparatus 600 becomes fixed. This makes it possible to aim the laser ray irradiation at the target point within the target area more securely and easily. Moreover, the pressure generated due to the expansion of the balloon 630 is applied to the deep area of the tissue through the surface of the tissue. This causes shortening of the laser ray path from the irradiating unit 611 to the target point, which in turn causes reduction of energy loss, or energy absorption by the tissue so that it becomes possible to heat the target point to achieve a desired temperature with a lower energy level of the laser ray. Moreover, it becomes possible to prevent the damage of the surface layer more securely as the surface layer of the tissue, or the area that makes contact with the balloon 630 and its vicinity is cooled by the working fluid.

When the working fluid is circulated, the working fluid is fed from the inlet connector and discharged through the outlet connector. More specifically, the working fluid fed through the inlet connector flows into the balloon 630 via the feeding lumen. The working fluid circulates through the balloon 630 and is discharged through the outlet connector via the discharging lumen after circulating at least half way.

When the laser irradiation at the target area is completed, the flow of the working fluid through the inlet connector is stopped and only the discharge of the working fluid through the outlet connector is executed. As the working fluid in the balloon 630 is discharged through the outlet connector via the discharging lumen, the balloon 630 contracts. The body 610 is removed from the celom while the balloon is contracted.

The position and direction of the apparatus 600 is fixed more easily and securely as mentioned before by means of the balloon 630. Moreover, in the apparatus 600, the surface layer of the tissue is cooled with the working fluid in the balloon 630.

It is also possible to form a lubricating coated layer on the surface of the balloon 630 as in the Embodiment 4. It is also possible to provide a balloon in case of the laser ray irradiation apparatuses 400, 500 of the Embodiments 4, 5.

Embodiment 7

Figure 24:
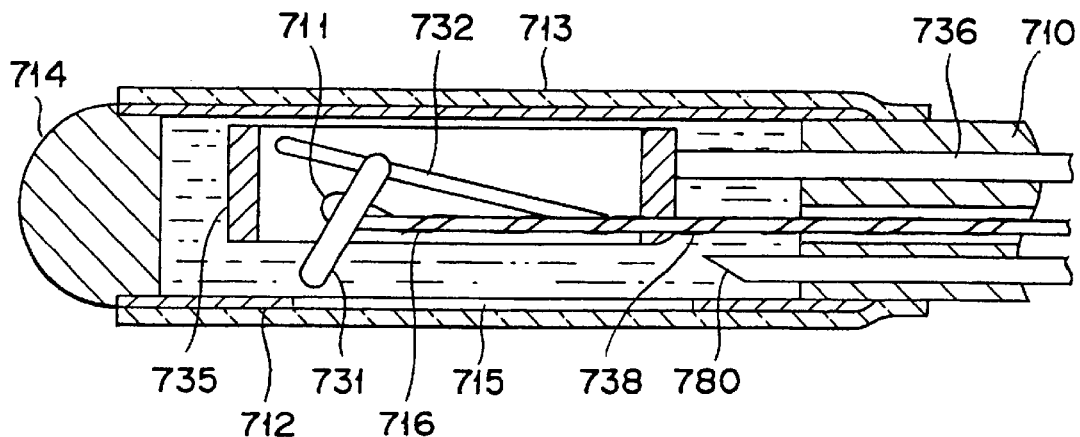
FIG. 24 is a cross section of a distal end of an ultrasonic irradiation apparatus of a seventh embodiment of the present invention.

An energy irradiation apparatus 700 shown in FIG. 24 is a lateral irradiating type ultrasonic ray irradiation apparatus typically used for the treatment of Benign Prostatic Hyperplasia and various tumor such as cancer by applying an ultrasonic ray into a tissue. Only the differences from the Embodiment 4 through the Embodiment 6 will be discussed in the following, skipping points of similarities.

The ultrasonic ray irradiation apparatus 700 includes a body 710 of a long shape, an irradiating unit 711 having an oscillator 731, which is an ultrasonic transducer that converts electric energy into ultrasonic ray, arms 716 that supports the irradiating unit 711, and an ultrasonic endoscope 780. The structure and actions of a positioning rod 736 and a rail member 735 that have grooves (guide) 732 and moves in the axial direction of the body 710, and a positioning rod 736 are similar to the Embodiment 5 and the Embodiment 6. The apparatus 700 further includes a pair of lead wires 738 with an insulating coated layer to supply electric power to the oscillator 731. The lead wire 738 is arranged to be wrapped around the arm 716. The housing 712 contains in the inside an ultrasonic ray transmitting substance such as physiological saline. Therefore, the ultrasonic ray of the endoscope 780 and the ultrasonic ray generated by the oscillator 731 are effectively transmitted to the outside of the housing 712.

A frequency of the ultrasonic ray cannot be determined indiscriminately as it varies with the type of organ where the lesional region exists, the location, depth and range of the lesional region. However, it is preferable to use the ultrasonic ray having the frequency in the range of 1 MHz to 50 MHz for the soft tissue located about 1 cm to 5 cm below the surface layer of the tissue.

The endoscope 780 is of an oblique viewing, is detachable from the apparatus 700, and is inserted from the proximal end of the apparatus 700. It is possible to observe the position irradiated by the ultrasonic ray irradiating unit 711, the irradiating direction and the irradiated surface condition by means of the endoscope 780. In other words, irradiation to improper areas can be prevented as the target area position can be confirmed accurately by means of the endoscope 780.

Moreover, the irradiation condition can be arbitrarily changed as the irradiated surface condition can be observed continuously during the irradiation of the ultrasonic ray.

The movements of the irradiating unit in the Embodiment 4 through the Embodiment 8 are controlled in the interlocking activities between the transporting device (arm) and the guide (grooves) fixed during the irradiation. In other words, changes of the reciprocating movement and the tilting angle of the irradiating unit are realized by the transporting device consisting of a single bar-like member. Therefore, the structure of the apparatus is simple, the manufacture of the apparatus is easier, and the possibility of the apparatus' malfunction is small.

Moreover, if an adjusting device such as the positioning rod or the joint and groove is provided to change the guide position or the mounting location of the rod, the target point position can be changed without moving the body. In this case, the entire target area can be heated uniformly to a desired temperature while maintaining the temperatures of the areas other than the target area at relatively low temperatures. In other words, the operation is easier and the patient's stress can be reduced.

Embodiment 8

Figure 25:
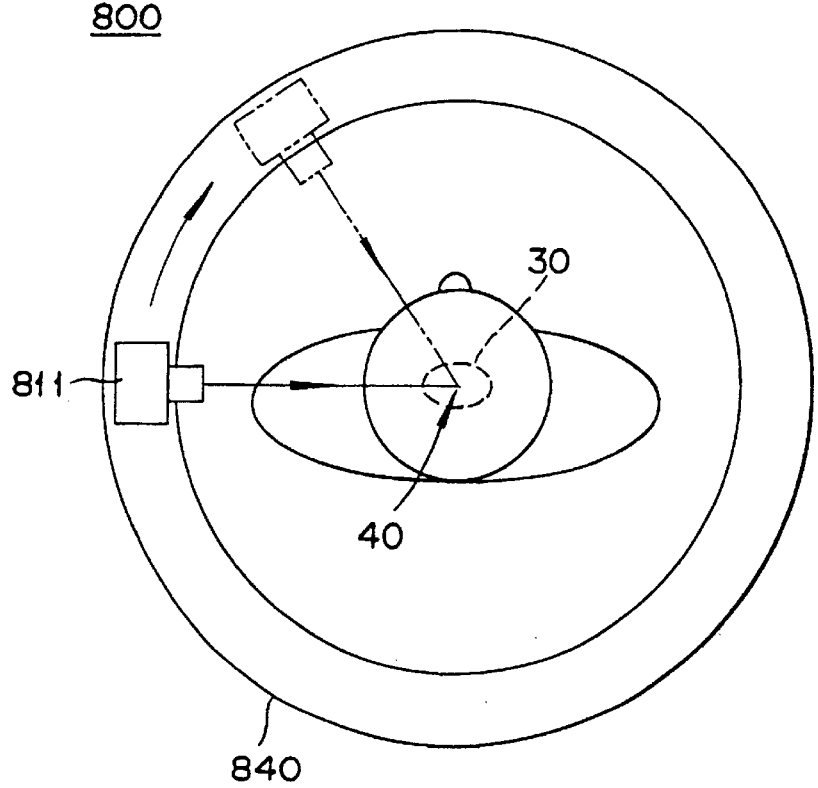
FIG. 25 is a plan view of a gamma ray irradiation apparatus of an eighth embodiment of the present invention.

An energy irradiation apparatus 800 shown in FIG. 25 is a gamma ray irradiation apparatus typically used for the treatment of cerebrovascular disease and intracerebral disease such as brain tumor by applying an ultrasonic ray into a tissue. The bodies of the energy irradiation apparatuses related to the Embodiment 1 through the Embodiment 7 are inserted into the celom to treat the lesional region in the neighborhood of the celom. On the other hand, the gamma ray irradiation apparatus 800 is externally disposed to treat the lesional region 30.

The gamma ray irradiation apparatus 800 includes an irradiating unit 811 with a cobalt-60 radiation source for radiating the gamma ray, and a ring-shaped rail 840 for moving the irradiating unit 811. The center of the rail 840 is located at a target point 40 of a target area 30, or the lesional region in the brain. Therefore, by moving the irradiating unit 811 along the rail 840 while the gamma ray is radiated from the irradiating unit 811, the gamma ray constantly passes through the target point 40. In other words, the gamma ray can be used to treat only the deep lesional region while protecting other area of normal tissue in tact. A linear motor can be used as the drive source of the irradiating unit 811.

Embodiment 9

Figure 26:
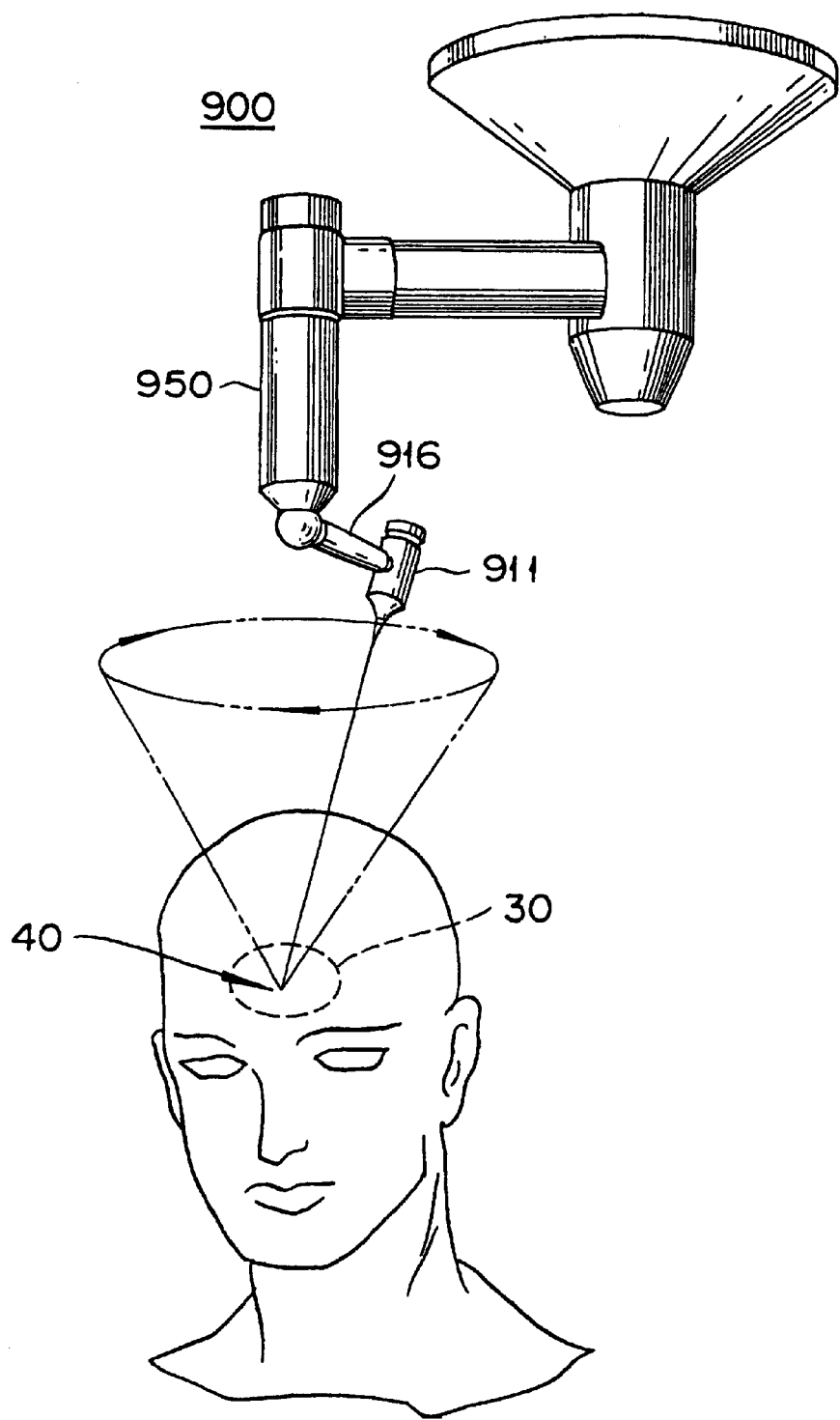
FIG. 26 is a perspective view of a gamma ray irradiation apparatus of a ninth embodiment of the present invention.

An energy irradiation apparatus 900 shown in FIG. 26 is a gamma ray irradiation apparatus similar to the Embodiment 8. Only the differences from the Embodiment 8 will be discussed in the following, skipping points of similarities.

The gamma ray irradiation apparatus 900 includes a irradiating unit 911 with a cobalt-60 radiation source for radiating the gamma ray, and a drive unit 950 that is interlocked with the irradiating unit 911 via an arm 916. The irradiating unit 911 is rotated around the axis of the drive unit 950 which is connected to a motor. Different from the Embodiment 8, the path of gamma ray is not on a single plane but changes. In other words, the path of the gamma rays forms a cone and the gamma ray constantly passes through the apex 40 of the cone, or a target point 40 of a target area 30 in the brain. Therefore, even when an obstacle exists adjacent to the surface layer of the tissue surrounding the lesional region 30 so that it is difficult to use the apparatus 800 of the Embodiment 8, the present apparatus

900 can be easily applied. It is suitable for treatment of disease in the abdominal region, for example.

It is obvious that this invention is not limited to the particular embodiments shown and described above but may be variously changed and modified by any person of ordinary skill in the art without departing from the technical concept of this invention.

For example, the constitution of each part can be replaced with any constitution that provides a similar function. Also, the features of each embodiment mentioned above can be combined. Specifically, the endoscopes 180, 380 used in the Embodiments 1, 3 can be used for the Embodiment 2. The balloon 230 used in the Embodiment 2 can be used for the Embodiments 1, 3. The ultrasonic transducer 731 used in the Embodiment 7 is applicable in the Embodiment 4 through the Embodiment 6. The balloon 630 used in the Embodiment 6 is applicable to the Embodiments 4, 5 and 7.

Further, the entire disclosure of Japanese Patent Application No. 10-148023 filed on May 28, 1998 and Japanese Patent Application No. 10-165423 filed on Jun. 12, 1998 including the specification, claims, drawings and summary is incorporated herein by reference in its entirety.

What is claimed is:

1. An energy irradiation apparatus comprising:
   an irradiating unit for radiating an energy with a deep transmitting capability against a tissue;
   a transporting device for transporting said irradiating unit within a predetermined area; and
   an interlocking device for changing irradiation angle in response to transportation of said irradiating unit so that the energy radiated by said moving irradiating unit always passes through an area which is smaller than the predetermined area.

2. An apparatus in accordance with claim 1, in which said irradiating unit is provided on a body of a long shape and radiates the energy in a direction perpendicular to or at an angle to an axis of the body, and said transporting device moves said irradiating unit parallel to the axis of the body.

3. An apparatus in accordance with claim 2, in which said transporting device is connected to an electrical drive device to reciprocate said irradiating unit relative to the axis of the body.

4. An apparatus in accordance with claim 2, further comprising an adjusting device for adjusting an interlocking relation between said irradiating unit's position and angle, which are determined by said interlocking device.

5. An apparatus in accordance with claim 2, wherein said apparatus is connectable to an energy generating device.

6. An apparatus in accordance with claim 5, further comprising an energy transmitting member that transmits energy from the energy generating device to said irradiating unit.

7. An apparatus in accordance with claim 6, further comprising an optical element that converges the energy consisting of laser ray between a distal end of said energy transmitting member and said irradiating unit.

8. An apparatus in accordance with claim 6, in which said energy transmitting member moves together with said irradiating unit.

9. An apparatus in accordance with claim 8, further comprising a shock absorbing device for absorbing motion of said energy transmitting member.

10. An apparatus in accordance with claim 5, in which said irradiating unit has a reflecting surface to reflect energy from the energy generating device.

11. An apparatus in accordance with claim 10, in which said reflecting surface is concave.

12. An apparatus in accordance with claim 2, further comprising a guide non-parallel to the axis of the body, a portion of said irradiating unit engaging with said guide in such a way that it can slide freely.

13. An apparatus in accordance with claim 12, in which said transporting device is connected to an electrical drive device to reciprocate said irradiating unit relative to the axis of the body.

14. An apparatus in accordance with claim 13, further comprising an adjusting device for adjusting a movement of reciprocating motion of said irradiating unit, said transporting device consisting of a single rod-like member.

15. An apparatus in accordance with claim 12, in which said guide is capable of moving parallel to the axis of the body.

16. An apparatus in accordance with claim 12, wherein said apparatus is connectable to an energy generating device.

17. An apparatus in accordance with claim 16, further comprising an energy transmitting member that transmits energy from the energy generating device to said irradiating unit.

18. An apparatus in accordance with claim 17, further comprising an optical element that converges the energy consisting of laser ray between a distal end of said energy transmitting member and said irradiating unit.

19. An apparatus in accordance with claim 16, in which said irradiating unit has a reflecting surface to reflect energy from the energy generating device.

20. An apparatus in accordance with claim 2, wherein said body comprises a lumen into which an endoscope is removably inserted.

* * * * *